(12) United States Patent
Fahrig et al.

(10) Patent No.: US 6,589,941 B1
(45) Date of Patent: Jul. 8, 2003

(54) UTILIZATION OF 5' SUBSTITUTED NUCLEOSIDES FOR RESISTANCE FORMATION IN CYTOCLASTIC TREATMENT, AND DRUG CONTAINING THESE NUCLEOSIDES, POLYMERS, METHODS OF USE AND COMPOSITIONS

(75) Inventors: Rudolf Fahrig, Hannover (DE); Angela Steinkamp-Zucht, Hannover (DE)

(73) Assignee: Resprotect GmbH, Dresden (DE)

( * ) Notice: Subject to any disclaimer, the term of this patent is extended or adjusted under 35 U.S.C. 154(b) by 0 days.

(21) Appl. No.: 09/520,901

(22) Filed: Mar. 7, 2000

Related U.S. Application Data

(63) Continuation-in-part of application No. 08/875,491, filed as application No. PCT/DE96/00169 on Jan. 31, 1996, now abandoned.

(30) Foreign Application Priority Data

Feb. 1, 1995  (DE) .......................................... 195 03 152
Dec. 8, 1995  (DE) .......................................... 195 45 892

(51) Int. Cl.$^7$ .......................... A01N 43/04; A61K 31/70
(52) U.S. Cl. ............................. 514/50; 514/51; 514/52; 514/974
(58) Field of Search ............................. 514/50, 51, 52, 514/974

(56) References Cited

U.S. PATENT DOCUMENTS

| | | | |
|---|---|---|---|
| 4,894,365 A | * | 1/1990 | De Clercq et al. ............ 514/50 |
| 4,902,678 A | * | 2/1990 | Smith |
| 4,988,678 A | * | 1/1991 | De Clercq et al. ............ 514/50 |
| 5,250,296 A | | 10/1993 | Ootsu |
| 5,831,064 A | | 11/1998 | Chang et al. |
| 6,011,000 A | * | 1/2000 | Perrine et al. |
| 6,245,750 B1 | | 6/2001 | Shepard |

FOREIGN PATENT DOCUMENTS

| | | |
|---|---|---|
| BE | 640236 | 3/1964 |
| EP | 488718 | 6/1992 |
| GB | 1473148 | 5/1977 |

OTHER PUBLICATIONS

Keizer et al. Journal of Cancer Research and Clinical Oncology (1994). vol. 120, No. 9, pp. 545–549, (Abstract), 1994.*

Iigo et al. Japanese Journal of Cancer Research; vol. 81, No. 4 pp. 431–435, 1990.*

Murray D. Norris, et al., "Expression of the Gene for Multidrug–Resistance–Associated Protein and Outcome in Patients with Neuroblastoma", MRP Gene Expression and Prognosis in Neuroblastoma, vol. 334, No. 4, pp. 231–238 (Jan. 1996).

M. Volm, et al., "Time Course of MDR Gene Amplification During in Vivo Selection for Doxorubicin–Resistance and During Reversal in Murine Leukemia L 1210", Anticancer Research, 11, pp. 579–585 (1991).

Robert T. Schimke, "Gene Amplification, Drug Resistance, and Cancer", Cancer Research, 44, pp. 1735–1742 (May 1984).

Piotr Chomczynski et al., "Single–Step Method of RNA Isolation by Acid Guanidinium Thiocyanate–Phenol–Chloroform Extraction", Analytical Biochemistry, 162, pp. 156–159 (1987).

James M. Ford, et al., "Pharmacology of Drugs that Alter Multidrug Resistance in Cancer", Pharmacological Reviews, vol. 42, No. 3, pp. 155–199 (1990).

A. Livingstone, et al., "N–myc Gene Copy Number in Neuroblastoma Cell Lines and Resistance to Experimental Treatment", European Journal of Cancer, vol. 30A, No. 3, pp. 382–389 (1994).

Michieli et al., "mdr–1 Gene Amplification in Acute Lymphoblastic Leukaemia Prior to Antileukaemic Treatment", Br. J. Haematol., vol. 78, pp. 288–289 (1991).

Lavi, "Carcinogen–mediated Amplification of viral DNA Sequences in Simian Virus 40–Transformed Chinese Hamster Embryo Cells", Proc. Natl. Acad. Sci, vol. 78, No. 10, pp. 6144–6148 (1981).

Demidova et al., "Gene Amplification in Murine Leukemia Cells with Multiple Drug Resistance Acquired in vivo", Genetika, vol. 23 (10), pp. 1797–1806 (1987), with an English language Abstract.

Liu, "Oncogene Expression in Adriamycin and Platinum Resistant Cell Lines", Chung Hua I Hseuh Tsa Chih, vol. 73, pp. 552–554 (1993), with an English language Abstract.

Iigo et al., *Jpn. J. Cancer Res.* 81, 431–435 (Apr. 1990).

Chakrabartty et al., "Loss of Plasmid Linked Drug Resistance after Treatment with Iodo–deoxyuridine", *Indian Journal of Experimental Biology*, 22, pp. 333–334 (1984).

Locarnini, "Hepatitis B Antiviral Therapy", *Today's Life Science*, pp. 32,34,36–38 and 80 (1990).

Wildiers, "Oral (E)–5–(2–Bromovinyl)–2'–Deoxyuridine Treatment of Severe Herpes zoster in Cancer Patients", *European Journal of Cancer & Clinical Oncology*, 20, pp. 471–476 (1984).

(List continued on next page.)

*Primary Examiner*—James O. Wilson
*Assistant Examiner*—Patrick Lewis
(74) *Attorney, Agent, or Firm*—Greenblum & Bernstein, P.L.C.

(57) ABSTRACT

The invention relates to a method of producing a composition and to a composition for preventing or reducing formation of resistance in cytostatic treatment comprising combining BVDU, a salt thereof or BVDU in protected form or in prodrug form with at least one cytostatic agent in order to prevent or reduce the formation of resistance during cytostatic treatment. The present invention is also directed to a method of reducing resistance in cytostatic treatment comprising delivering therapeutically-effective amount of at least one cytostatic agent and a therapeutically effective amount of BVDU, a salt thereof, or BVDU in protected form or in prodrug form.

53 Claims, 15 Drawing Sheets

OTHER PUBLICATIONS

Chi et al., "Iododeooxyuridine Chemosensitization of cis–Diamminedichloroplatinum(II) in Human Bladder Cancer Cells", *Cancer Research*, 54, pp. 2701–2706 (1994).

Wroblewski et al., "The Possible Role of Altered Nucleotide Metabolism in Cisplatin Resistance", *J. Cell Pharmacol.*, 1 pp. 2–7 (1990).

Hirohashi et al., "Genetic Alterations in Human Gastric Cancer", *Cancer Cells*, 3, pp. 49–52 (1991).

Sasano et al., "Protooncogene Amplification and Tumor Ploidy in Human Ovarian Neoplasms", *Human Pathology*, 21, pp. 382–391 (1990).

Borg et al., "'c–myc Amplification is an Independent Prognostic Factor in Postmenopausal Breast Cancer", *Int. J. Cancer*, 51, pp. 687–691 (1992).

Borg et al., "Association of INT2/HST1 Coamplification in Primary Breast Cancer with Hormone–Dependent Phenotype and Poor Prognosis", Br. J. Cancer, 63, pp. 136–142 (1991).

Descotes et al., "Human Breast Cancer: Correlation Study Between HER–2/neu Amplification and Prognostic Factors in an Unselected Population", *Anticancer Research*, 13, pp. 119–124 (1993).

Klijn et al., "The Clinical Significance of Epidermal Growth Factor Receptor (EGF-R) in Human Breast Cancer: A Review on 5232 Patients", *Endocrine Reviews*, 13, pp. 3–17 (1992).

Tsuda et al., "High Incidence of Coamplification of hst–1 and int–2 Genes in Human Esophageal Carcinomas", *Cancer Research*, 49, pp. 5505–5508 (1989).

Kennedy, "Prevention of Carcinogenesis by Protease Inhibitors", Cancer Research (Suppl.), 54, pp. 1999's –2005s (1994).

Troll et al., "Tumorigenesis in Mouse Skin: Inhibition by Synthetic–Inhibitiors of Proteases", *Science*, 169, pp. 1211–1213 (1970).

Moscow et al., "Multidrug Resistance", *Journal of the National Cancer Institute*, 80, pp. 14–20 (1988).

Oshiro et al., "Genotoxic Properties of (E)–5–(2–Bromovinyl)–2'–deoxyuridine (BVDU)", *Fundamental and Applied Toxicology*, 18, pp. 491–498 (1992).

"Red List 1995", Editio Cantor Verlag fur Medizin und Naturwissenschaften, Aulendorf/Wurtt (1995).

Sharon B. Bordow, et al., "Expression of the Multidrug Resistance–Associated Protein (MRP) Gene Correlates with Amplification and Overexpression of the N–myc Oncogene in Childhood Neuroblastoma", Cancer Research, 54, pp. 5036–5040 (Oct. 1994).

Alok Bhushan et al., "Expression of c–fos in Human and Murine Multidrug–Resistant Cells", Molecular Pharmacology, 42, pp. 69–74 (1992).

Alok Bhushan, et al., "Expression of c–fos Precedes MDR3 in Vincristine and Adriamycin Selected Multidrug Resistant Murine Erythroleukemia Cells", Biochemical and Biophysical Research Communications, 226, pp. 819–821 (1996).

Thomas Braun, et al., "Differential Expression of Myogenic Determination Genes in Muscle Cells: Possible Autoactivation by the Myf Gene Products", EMBO Journal, vol. 8, No. 12, pp. 3617–3625 (1989).

Rudolf Fahrig, "Anti–Recombinogenic and Convertible Co–Mutagenic Effects of (E)–5–(2–bromovinyl)–2'–deoxyuridine (BVDU) and Other 5–substituted Pyrimidine Nucleoside Analogs in *S. cerevisiae* MP1", Mutation Research, 372, pp. 133–139 (1996).

Rudolf Fahrig, et al., "Induction or Suppression of SV40 Amplification by Genotoxic Carcinogens, Non–Genotoxic Carcinogens or Tumor Promoters", Mutation Research, 356, pp. 217–224 (1996).

Roy A. Frye, et al., "Detection of Amplified Oncogenes by Differential Polymerase Chain Reaction", Oncogene, 4, pp. 1153–1157 (1989).

Michael M. Gottesman, "How Cancer Cells Evade Chemotherapy: Sixteenth Richard and Hinda Rosenthal Foundation Award Lecture", Cancer Research, 53, pp. 747–754 (1993).

A. V. Gudkov, et al., "Karyotype and Amplicon Evolution During Stepwise Development of Multidrug Resistance in Djungarian Hamster Cell Lines", in I.B. Roninson (ed.), Molecular and Cellular Biology of Multidrug Resistance in Tumor Cells, pp. 147–168 (Plenum, New York 1991).

Roberts H. Haynes, "Molecular Mechanisms in Genetic Stability and Change: The Role of Deoxyribonucleotide Pool Balance", in F.J. de Serres (Ed.), Genetic Consequences of Nucleotide Pool Imbalance, pp. 1–23 (Plenum, New York 1985).

Stephen I–Hong Hsu, et al., "Differential Overexpression of Three mdr Gene Family Members in Multidrug–resistant J774.2 Mouse Cells", Journal of Biological Chemistry, vol. 264, No. 20, pp. 12053–12062 (1989).

Stephen I–Hong Hsu, et al., "Structural Analysis of the Mouse mdrla (P–Glycoprotein) Promoter Reveals the Basis for Differential Transcript Heterogeneity in Multidrug–Resistant J774.2 Cells", Molecular and Cellular Biology, vol. 10, No. 7, pp. 3596–3606 (1990).

Bernard A. Knuz, et al., "Deoxyribonucleoside Triphosphate Levels: A Critical Factor in the Maintencnce of Genetic Stability", Mutation Research, 318, pp. 1–64 (1994).

Akira Nakagawara, et al., "Inverse Correlation Between Expression of Multidrug Resistance Gene and N–myc Oncogene in Human Neuroblastomas", Cancer Research, 50, pp. 3043–3047 (1990).

Murray D. Norris, et al., "Expression of the Gene for Multidrug–Resistance—Associated Protein and Outcome in Patients with Neuroblastoma", New England Journal of Medicine, vol. 334, No. 4, pp. 231–237 (1996).

W. Ostertag, et al., "Duplicated –Chain Genes in Hopkins–2 Haemoglobin of Man and Evidence for Unequal Crossing Over Between Them", Nature New Biology 237, pp. 90–94 (1972).

András Schaefer, et al., "Decreased Resistance to N,N–dimethylated Anthracyclines in Multidrug–Resistant Friend Erythroleukemia Cells", Cancer Chemotherapy and Pharmacology, 31, pp. 301–307 (1993).

Robert T. Schimke et al., "Overreplication and Recombination of DNA in Higher Eukaryotes: Potential Consequences and Biological Implications", Proc. Natl. Acad. Sci., 83, pp. 2157–2161 (1986).

Fredric C. Vokert, et al., "Site–Specific Recombination Promotes Plasmid Amplification in Yeast", Cell, 46, pp. 541–550 (1986).

Geoffrey M. Wahl, "The Importance of Circular DNA in Mammalian Gene Amplification", Cancer Research, 49, pp. 1333–1340 (1989).

Petra Winkelmeier, "Quantification of Cytotoxicity by Cell Volume and Cell Proliferation", ATLA, 21, pp. 269–280 (1993).

John Brennan, et al., "myc Family DNA Amplification in 107 Tumors and Tumor Cell Lines from Patients with Small Cell Lung Cancer Treated with Different Combination Chemotherapy Regimens", Cancer Research, 51, pp. 1708–1712 (1991).

Claude Desgranges, et al., "Regeneration of the Antiviral Drug (E)–5–(2–bromovinyl)–2'–deoxyuridine in vivo", Nucleic Acids Research, vol. 12, No. 4, pp. 2081–2090 (1984).

Jan Olgemöller et al., "Determination of (E)–5–(2–bromovinyl)–2'–deoxyuridine in Plasma and Urine by Capillary Electrophoresis", Journal of Chromatography B, 726, pp. 261–268 (1999).

E. de Clercq, et al., "Pharmacokinetics of (E)–5–(2–Bromovinyl)–2'–Deoxyuridine in Mice", Antimicrobial Agents and Chemotherapy, vol. 16, No. 2, pp. 234–236 (1979).

Anne Livingstone, et al., "N–myc Amplification and its Relationship to Experimental Therapy", Journal of Neuro–Oncology, 31, pp. 33–39 (1997).

Pulivarthi H. Rao, et al., "Chromosomal Amplification Is Associated with Cisplatin Resistance of Human Male Germ Cell Tumors", Cancer Research, 58, pp. 4260–4263 (1998).

Alex d. Lewis, et al., "Amplification and Increased Expression of Alpha Class Gluthathione S–transferase–encoding Genes Associated with Resistance to Nitrogen Mustards", Proc. Natl. Acad. Sci., 85, pp. 8511–8515 (1988).

Tamar Kleinberger, et al., "Carcinogen–Mediated Methotrexate Resistance and Dihydrofolate Reductase Amplification in Chinese Hamster Cells", Molecular and Cellular Biology, vol. 6, No. 6, pp. 1958–1964 (1986).

Erich Gebhart, et al., "Cytogenetic Studies on Human Breast Carcinomas", Breast Cancer Research and Treatment, 8, pp. 125–138 (1986).

Bernard Dutrillaux, et al., "Characterization of Chromosomal Anomalies in Human Breast Cancer: A Comparison of 30 Paradiploid Cases with Few Chromosome Changes", Cancer Genet Cytogenet, 49, pp. 203–217 (1990).

Xin–Yuan Guan, et al., "Identification of Cryptic Sites of DNA Sequence Amplification in Human Breast Cancer by Chromosome Microdissection", Nature Genetics, 8, pp. 155–161 (1994).

Martine Muleris, et al., "Detection of DNA Amplification in 17 Primary Breast Carcinomas With Homogeneously Staining Regions by a Modified Comparative Genomic Hybridization Technique", Genes, Chromosomes and Cancer 10, pp. 160–170 (1994).

Joyce L. Hamlin, et al., "The Mammalian Dihydrofolate Reductase Locus", Biochimica et Biophysica Acta, 1087, pp. 107–125 (1990).

M. Kashani–Sabet, et al., "Detection of Drug Resistance in Human Tumors by in Vitro Enzymatic Amplification", Cancer Research, 48, pp. 5775–5778 (1988).

Gian Paolo Tonini, et al., "Antiblastic Treatment does not Affect N–myc Gene Amplification in Neuroblastoma", Anticancer Research, 7, pp. 729–732 (1987).

Akira Nakagawara, et al., "Inverse Correlation Between Expression of Multidrug Resistance Gene and N–myc. Oncogene in Human Neuroblastomas", Cancer Research, 50, pp. 3043–3047 (1990).

Sharon B. Bordow, et al., "Expression of the Multidrug Resistance–associated Protein (MRP) Gene Correlates with Amplification and Overexpression of the N–myc Oncogene in Childhood Neuroblastoma", Cancer Research, 54, pp. 5036–5040 (1994).

Mohammed Kashani–Sabet, et al., "Differential Oncogene Amplification in Tumor Cells from a Patient Treated with Cisplatin and 5–Fluorouracil", Eur. J. Cancer, vol. 26, No. 3, pp. 383–390 (1990).

Marshall D. Sklar, et al., "Modulation of cis–Platinum Resistance in Friend Erythroleukemia Cells by c–myc", Cancer Research, 51, pp. 2118–2123 (1991).

Hiroyuki Yamazaki, et al., "Oncogene Overexpression and De Novo Drug–Resistance in Human Prostate Cancer Cells", Biochimica et Biophysica Acta, 1226, pp. 89–96 (1994).

Åke Borg, et al., "ERBB2 Amplification is Associated with Tamoxifen Resistance in Steroid–Receptor Positive Breast Cancer", Cancer Letters, 81, pp. 137–144 (1994).

Hyung Ju C. Shin, et al., "Study of Multidrug Resistance (mdr1) Gene in Non–Small–Cell Lung Cancer", Anticancer Research, 12, pp. 367–370 (1992).

Anna B. Hill, et al., "Increased Gene Amplification in L5178Y Mouse Lymphoma Cells with Hydroxyurea–induced Chromosomal Aberrations", Cancer Research, 44, pp. 5050–5057 (1985).

Rudolf Fahrig, "Evidence that Induction and Suppression of Mutations and Recombinations by Chemical Mutagens in *S. cerevisia* During Mitosis are Jointly Correlated", Molec. gen. Genet., 168, pp. 125–139 (1979).

Rudolf Fahrig, "Genetic Mode of Action of Cocarcinogens and Tumor Promoters in Yeast and Mice", Molec. gen. Genet., 194, pp. 7–14 (1984).

Masamitsu Honma et al., "Recombinagenic Activity of the Phorbol Ester 12–O–tetradecanoylphorbol–13–acetate in Human Lymphoblastoid Cells", Carcinogenesis, vol. 16, No. 8, pp. 1717–1722 (1995).

Pawan K. Gupta, et al., "High Frequency in Vivo Loss of Heterozygosity Is Primarily a Consequence of Mitotic Recombination", Cancer Research, 57, pp. 1188–1193 (1997).

Pascale Bertrand, et al., "Increase of Spontaneous Intrachromosomal Homologous Recombination in Mammalian Cells Expressing a Mutant p53 Protein", Oncogene, 14, pp. 1117–1122 (1997).

Kristin L. Mekeel, et al., "Inactivation of p53 Results in High Rates of Homologous Recombination", Oncogene, 14, pp. 1847–1857 (1997).

Rudolf Fahrig, "Anti–Mutagenic Agents are also CO–Recombinogenic and can be Converted into Co–Mutagens", Mutation Research, 350, pp. 59–67 (1996).

Tapio Visakorpi, et al., "In vivo Amplification of the Androgen Receptor Gene and Progression of Human Prostate Cancer", Nature Genetics, 9, pp. 401–406 (1995).

Pasi Koivisto, et al., "Androgen Receptor Gene Amplificatio: A Novel Molecular Mechanism for Endocrine Therapy Resistance in Human Prostate Cancer", Scand. J. Clin. Lab. Invest., 56, Suppl. 226, pp. 57–63 (1996).

Rudolf Fahrig, "Effects of Bile Acids on the Mutagenicity and Recombinogenicity of Triethylene Melamine in Yeast Strains MP1 and D61.M", Arch. Toxicol., 60, pp. 192–197 (1987).

J. Wildiers, et al., "Oral (E)–5–(2–Bromovinyl)–2'–Deoxyuridine Treatment of Severe Herpes Zoster in Cancer Patients", Eur. J. Cancer Clin. Oncol., vol. 20, No. 4, pp. 471–476 (1984).

Y. Benoit, et al., "Oral BVDU Treatment of Varicella and Zoster in Children with Cancer", Eur. J. Prediatr., 143, pp. 198–202 (1985).

Jose Russo, et al., "Biology of Disease: Comparative Study of Human and Rat Mammary Tumorigenesis", Laboratory Investigation, vol. 62, No. 3, pp. 244–278 (1990).

Stefan Joos, et al., "Detection of Amplified DNA Sequences by Reverse Chromosome Painting Using Genomic Tumor DNA as Probe", Human Genetics, 90, pp. 584–589 (1993).

Anne Kallioniemi, et al., "Comparative Genomic Hybridization for Molecular Cytogenetic Analysis of Solid Tumors", Science, 258, pp. 818–821 (1992).

Olli–P. Kallioniemi, et al., "Optimizing comparative Genomic Hybridization for Analysis of DNA Sequence Copy Number Changes in Solid Tumors", Genes, Chromosomes and Cancer, 10, pp. 231–243 (1994).

Roland Kappler, et al., "Comparative Genomic in Situ Hybridization Discloses Chromosomal Copy Number Changes in a Transplanted Brain Tumor Line of the Rat", Mammalian Genome, 9, pp. 193–197 (1998).

Roland Kappler, et al., "Chromosomal Imbalances and DNA Amplifications in SV40 Large T Antigen–Induced Primitive Neuroectodermal Tumor Cell Lines of the Rat", Carcinogenesis, vol. 20, No. 8, pp. 1433–1438 (1999).

M. Volm, et al., "Time Course of MDR Gene Amplification During in Vivo Selection for Doxorubicin–Resistance and During Reversal in Murine Leukemina L 1210", AntiCancer Research, 11, pp. 579–586 (1991).

Robert T. Schimke, "Gene Amplification, Drug Resistance, and Cancer", Cancer Research, 44, pp. 1735–1742 (1984).

* cited by examiner

FIG.1
Relative DNA Content
DNA Amplification in Cells of the Chinese Hamster
Positive Control: Genotoxic Carcinogens
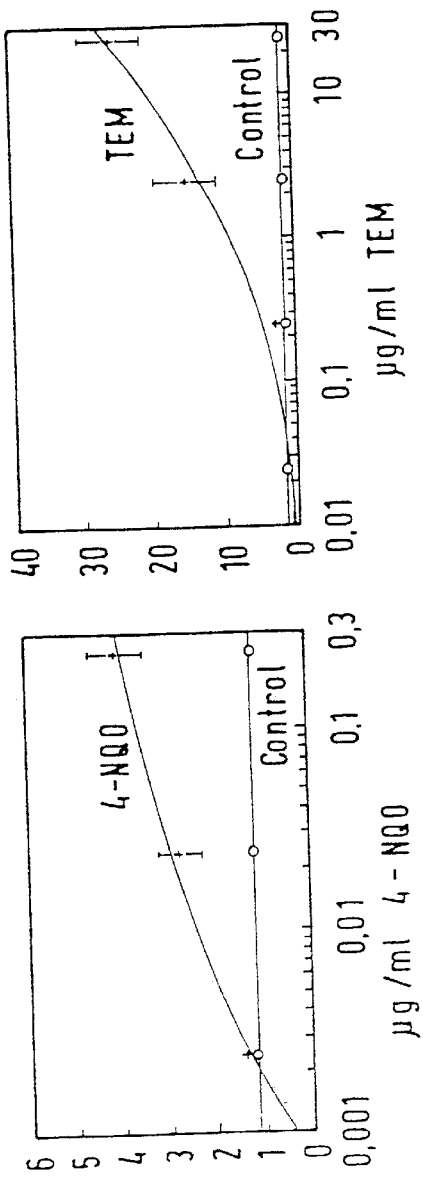
Negative Control: Non carcinogens
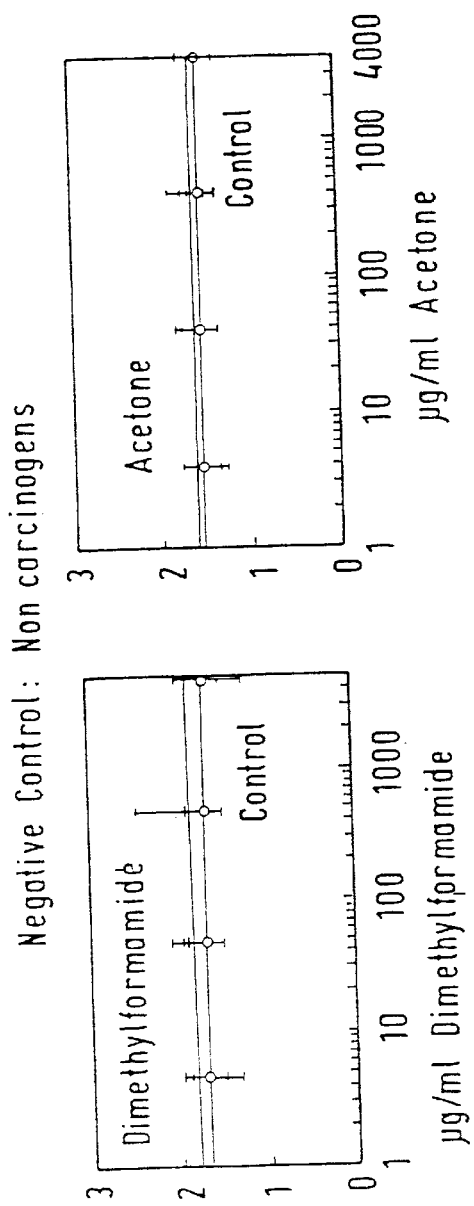

FIG.2
Relative DNA Content
DNA Amplification in Cells of the Chinese Hamster Tumour Inducers
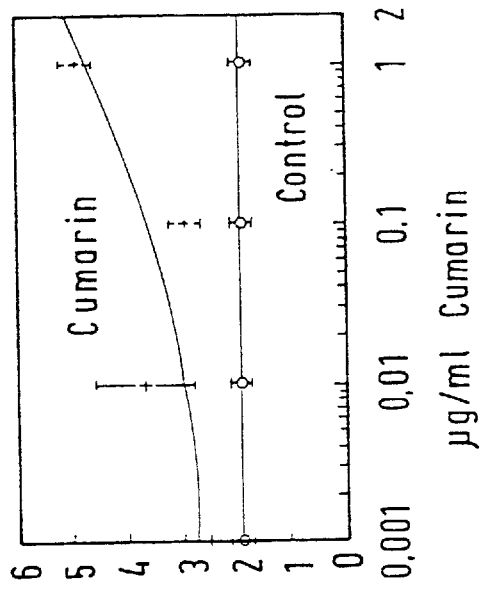
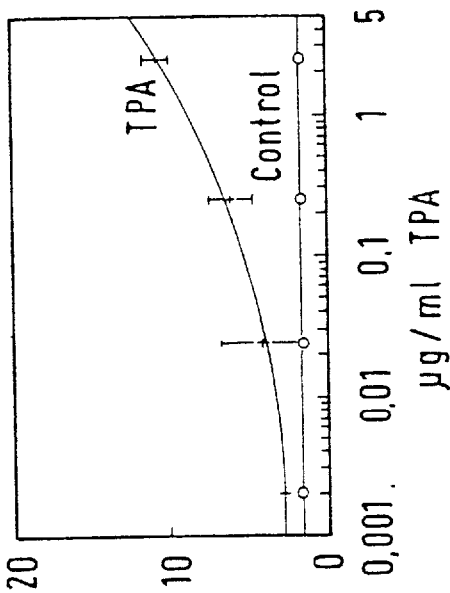
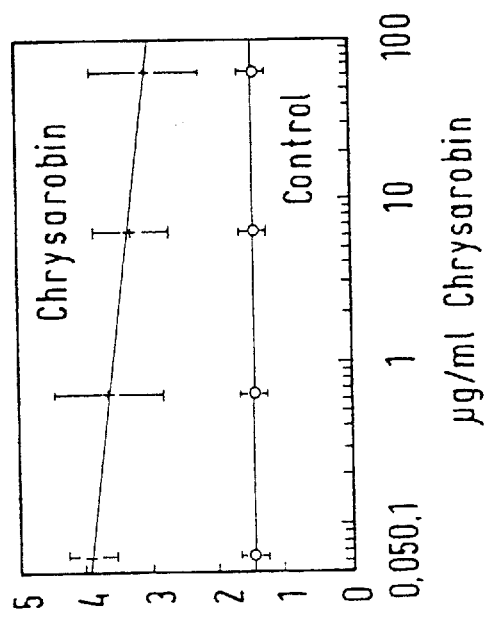
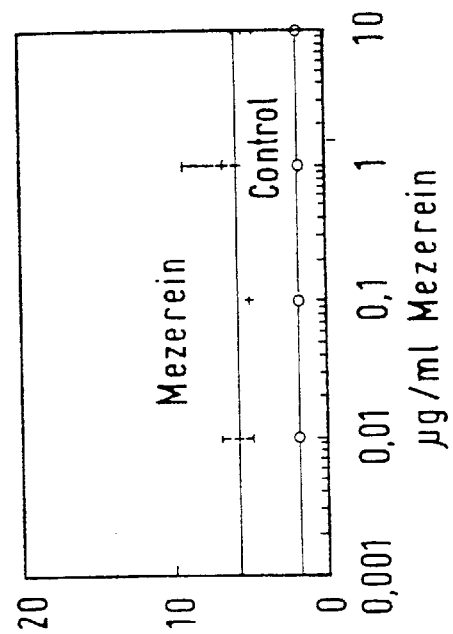

UTILIZATION OF 5' SUBSTITUTED NUCLEOSIDES FOR RESISTANCE FORMATION IN CYTOCLASTIC TREATMENT, AND DRUG CONTAINING THESE NUCLEOSIDES, POLYMERS, METHODS OF USE AND COMPOSITIONS

This application is a continuation-in-part of U.S. application Ser. No. 08/875,491, filed Oct. 14, 1997 now abandoned which is the national stage of PCT/DE96/00169, filed Jan. 31, 1996, which claims priority of German Application No. 195 45 892.3, filed Dec. 8, 1995 and German Application No. 195 03 152.0, filed Feb. 1, 1995. The present application expressly incorporates by reference herein the entire disclosures of U.S. application Ser. No. 08/875,491, filed Jan. 31, 1996, PCT/DE96/00169, filed Jan. 31, 1996, German Application No. 195 45 892.3, filed Dec. 8, 1995 and German Application No. 195 03 152.0, filed Feb. 1, 1995.

BACKGROUND OF THE INVENTION

1. Field of the Invention

The occurrence of "drug resistance" is the main reason for failure in cancer chemotherapy. Tumors which initially react sensitively to cytostatic agents very frequently recover after a certain treatment time and then are resistant to the effects of various types of antineoplastic drugs. Although the problem of "drug resistance" has been known since 1948 (the year when cancer therapy with cytostatic agents began), until now no way has been known of preventing the formation of resistance.

A characteristic of all highly resistant tumors and cell strains investigated to date is the amplification (multiplication) of a small group of genes. As a result of this DNA or gene amplification, an increased expression of these genes is exhibited, which can lead to resistance to the drug. As a result of this DNA amplification an increased expression of various genes occurs. Protective proteins which serve to shuttle toxins out of the cell can thus be formed in increased quantities (e.g., P-glycoprotein). This effect is also known as "multi-drug resistance" (MDR).

In addition to MDR, the degree of amplification of certain genes, especially certain oncogenes, correlates with the degree of malignancy. Thus, the chances of survival with an amplification of ERVV2, RASKI, INT3, HST1, MYC and KSRAM in stomach cancer are very poor. See Hirohasi, S., and Sugimura, T., "Genetic Alterations in Human Gastric Cancer, *Cancer cells* (Cold Spring Harbor), 3:49–52 (1991). The chances of survival with an amplification of and ERBB2 and MYC in ovarian carcinoma are also very poor. See Sasano, H., Garrett, C. T., Wilkinson, D. C., Silverberg, S., Comerford, J., and Hyde, J., "Protooncogene Amplification and Tumor Ploidy in Human Ovarian Neoplasm", *Hum. Pathol.*, 21:382–391 (1990).

In breast cancer, the amplification of MYC correlates with the progress of the disease. See Borg, A., Baldetorp, B., Fernö, M. Olsson, H., and Sigurdsson, H., "C-myc Amplification is an Independent Prognostic Factor in Postmenopausal Breast Cancer", *Int. J. Cancer*, 51:687–691 (1992). Likewise, in breast cancer, the coamplification of INT2 and HST1 correlates with the progress of the disease. See Borg, A., Sigurdsson, H., Clark, G. M., et al., "Association of INT2/HST1 Coamplification in Primary Breast Cancer with Hormone-Dependent Phenotype and Poor Prognosis", *Br.J.Cancer*, 63:136142 (1991).

The amplification of ERBB2 and EGFR is linked to a poor prognosis. See Descotes, F., Pavy, J. -J., and Adessi, G. L., "Human Breast Cancer: Correlation Study Between HER-2/neu Amplification and Prognostic Factors in an Unselected Population", *Anticancer Res.*, 13:119–124 (1993) and Klijn, J. G. M., Berns, P. M. J. J., Schmitz, P. I. M., and Foekens, J. A., "The Clinical Significance of Epidermal Growth Factor Receptor (EGF-R) in Human Breast Cancer: A Review on 5232 Patients", *Endocr.Rev.*, 13:3–17 (1992).

In esophageal cancer, the coamplification of HST1 and INT2 correlates with the degree of metastasis. See Tsuda, T., Tahara, E., Kajiyama, G., Sakamoto, H., Terada, M., and Sugimura, T., "High Incidence of Coamplification of HST-1 and INT-2 Genes in Human Esophageal Carcinomas", *Cancer Res.* 49:5505–5508, 1989).

In summary it can be ascertained that by means of chronic treatment with carcinogenic cytostatic agents, the induced gene amplification leads not only to resistance to this treatment, but also to the over-expression of certain oncogenes which control the degree of malignancy.

2. Discussion of Background

A series of substances have been described which counteract the acquired drug resistance. Included are those described in the work of Kennedy on the anti-carcinogenic effects of protease inhibitors. See Kennedy, A. R., "Prevention of Carcinogenesis by Protease Inhibitors", *Cancer Res.*, 54:1999–2005 (1994). These substances can suppress carcinogen-induced gene amplification to almost normal levels. Kennedy observed that radiation-induced gene amplification is suppressed in the same way corresponding with its capacity to suppress radiation-induced transformation, so that a relationship between these two processes can be assumed. In addition, protease-inhibitors act as antagonists of (co-recombinogenic) tumor inducers during the initiation of transformation in vitro. Protease-inhibitors are also described as effective anti-promoters in in vivo experiments. See Troll, W., Klassen, A., and Janoff, A., "Tumorigenesis in Mouse Skin: Inhibition by Synthetic Inhibitors of Proteases", *Science* (Washington D.C.) 169:1211–1213 (1970).

It is known that verapamil acts against MDR. See Moscow, I. A., and Cowan, K. H., "Multidrug Resistance", J. Natl. Cancer Inst., 80:14–20 (1988). This "calcium channel blocker" increases the cytotoxicity by increasing the intracellular accumulation of drugs, probably in part due to an effect on P-glycoprotein or other transport proteins. The toxicity of these and similar substances, such as quinidine, reduces their clinical usefulness.

SUMMARY OF THE INVENTION

In view of the foregoing, the present invention provides an effective substance for preventing or reducing resistance formation against treatment with cytostatic agents and provides for a corresponding drug. The present invention provides for a composition for preventing or reducing the formation of resistance in cytostatic treatment, the composition combining at least one 5' substituted nucleoside with at least one cytostatic agent.

The present invention provides for a method of producing a composition for preventing or reducing formation of resistance in cytostatic treatment comprising combining (E)-5-(2-bromovinyl-)2'-deoxyuridine (BVDU), a salt thereof, or BVDU in protected or in prodrug form with at least one cytostatic agent, which is an anti-carcinogenic agent and which is not 5-fluorouracil.

The present invention also provides for a composition for preventing or reducing the formation of resistance in cytostatic treatment comprising:

(E)-5-(2-bromovinyl-)2'-deoxyuridine (BVDU), a salt thereof, or BVDU in protected or in prodrug form, and at least one cytostatic agent, which is an anti-carcinogenic agent and which is not 5-fluorouracil, wherein the quantity of BVDU is effective to produce a concentration of 0.02 µg/ml to 10 µg/ml in blood.

The composition may also include at least one conventional carrier and may include at least one auxiliary material.

BVDU may be present in an amount effective to produce a concentration of 0.05 µg/ml to 5 µg/ml in blood.

Preferably, the at least one cytostatic agent may be selected from one or more of 20 alkaloids, alkylating agents, anti-metabolites, antibiotics, or cisplatin.

The present invention also provides for a method of reducing resistance in cytostatic treatment comprising delivering therapeutically-effective amount of at least one cytostatic agent, which is an anti-carcinogenic agent and which is not 5-fluorouracil, and therapeutically-effective amount of BVDU a salt thereof, or BVDU in protected or in prodrug form.

BVDU may be present in a therapeutically-effective amount, i.e., an amount effective to produce a blood concentration of BVDU from about 0.02 µg/ml to about 10 µg/ml. Preferably, BVDU is present in an amount effective to produce a blood concentration of from about 0.05 µg/ml to about 5 µg/ml.

The at least one cytostatic agent may be selected from one or more of alkaloids, alkylating agents, antibiotics, antimetabolites, hormonal agonists/antagonists or steroids and combinations.

The alkylating agents may be selected from one or more of bisulfan, carboplatin, cisplatin, melphalan, cyclophosphamide, ifosfamide, chloroambucil, mechlorethamine HCl, carmustine, lomustine, polifeprosan 20 or streptozocin sterile powder.

The antibiotics may be selected from one or more of doxorubicin hydrochloride, bleomycin sulfate, daunorubicin HCl, diactinomycin, daunorubicin citrate, doxorubicin HCl, idarubicin HCl, plicamycin, mitomycin, pentostatin, mitoxantrone, doxorubicin hydrochloride, or valrubicin.

The antimetabolites may be selected from one or more of cytarabine, fludarabine phosphate, floxuridine, cladribine, methotrexate, mercaptopurine, thioguanine, or capecitabine.

The hormonal agonists/antagonists may be selected from androgens, antiandrogens, antiestrogens, estrogen and nitrogen combinations, estrogens, gonadotropin releasing hormone (GNRH) analogues, progestins or immunomudulators.

The androgens may be selected from one or more of methyltestosterone, nilutamide, or testolactone.

The antiandrogens may be selected from one or more of bicalutamide or flutamide.

The antiestrogens may be selected from one or more of anastrozole, toremifene citrate, or tamoxifen citrate.

The the estrogen and nitrogen combinations is estramustine phosphate sodium.

The estrogens may be selected from one or more of ethinyl estradiol, esterified estrogen, or conjugated estrogen.

The GNRH analogues may be selected from one or more of leuprolide acetate or goserelin acetate.

The progestins may be selected from one or more of medroxyprogesterone acetate or magestrol acetate.

The immunomodulators may be selected from one or more of levamisole hydrochloride or aldesleukin.

The cytostatic agent may also be selected from one or more of allopurinol sodium, dolasetron mesylate, pamidronate disodium, etidronate disodium, fluconazole, erythropoietin, levamisole hydrochloride, amifostine, granisetron hydrochloride, leucovorin, sargramostim, dronabinol, 2-mercaptoethane sulfonate, filgrastim, octreotide acetate, pilocarpine hydrochloride, dexrazoxane, ondansetron hydrochloride, irinotecan hydrochloride, dacarbazine, asparaginase, etoposide phosphate, gemcitabine HCl, trastuzumab, altretarnine, topotecan hydrochloride, hydroxyurea, mitotane, interferon alfa-2b, procarbazine hydrochloride, vinorelbine tartrate, pegaspargase, vincaleukoblastine, 22-oxo, sulfate (1:1)(salt), denileukin diftitox, rituximab, aldesleukin, interferon alfa-2a, docetaxel, paclitaxel, BCG Live (Intravesical), BCG Live, vinblastine sulfate, etoposide, teniposide, or tretinoin.

The steroids and combinations may be selected from one or more of cortisone acetate, dexamethasonel, dexamethasone acetate, betamethasone sodium phosphate and betamethasone, hydrocortisone, hydrocortisone sodium phosphate, prednisolone sodium phosphate, prednisolone or methylprednisolone sodium succinate Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 1 shows the DNA amplification in cells from Chinese Hamster wherein the positive control is genotoxic carcinogens, and the negative control is non-carcinogens.

FIG. 2 shows the DNA amplification in cells from Chinese Hamster using tumor inducers.

DETAILED DESCRIPTION OF THE PRESENT INVENTION

Figure 3:
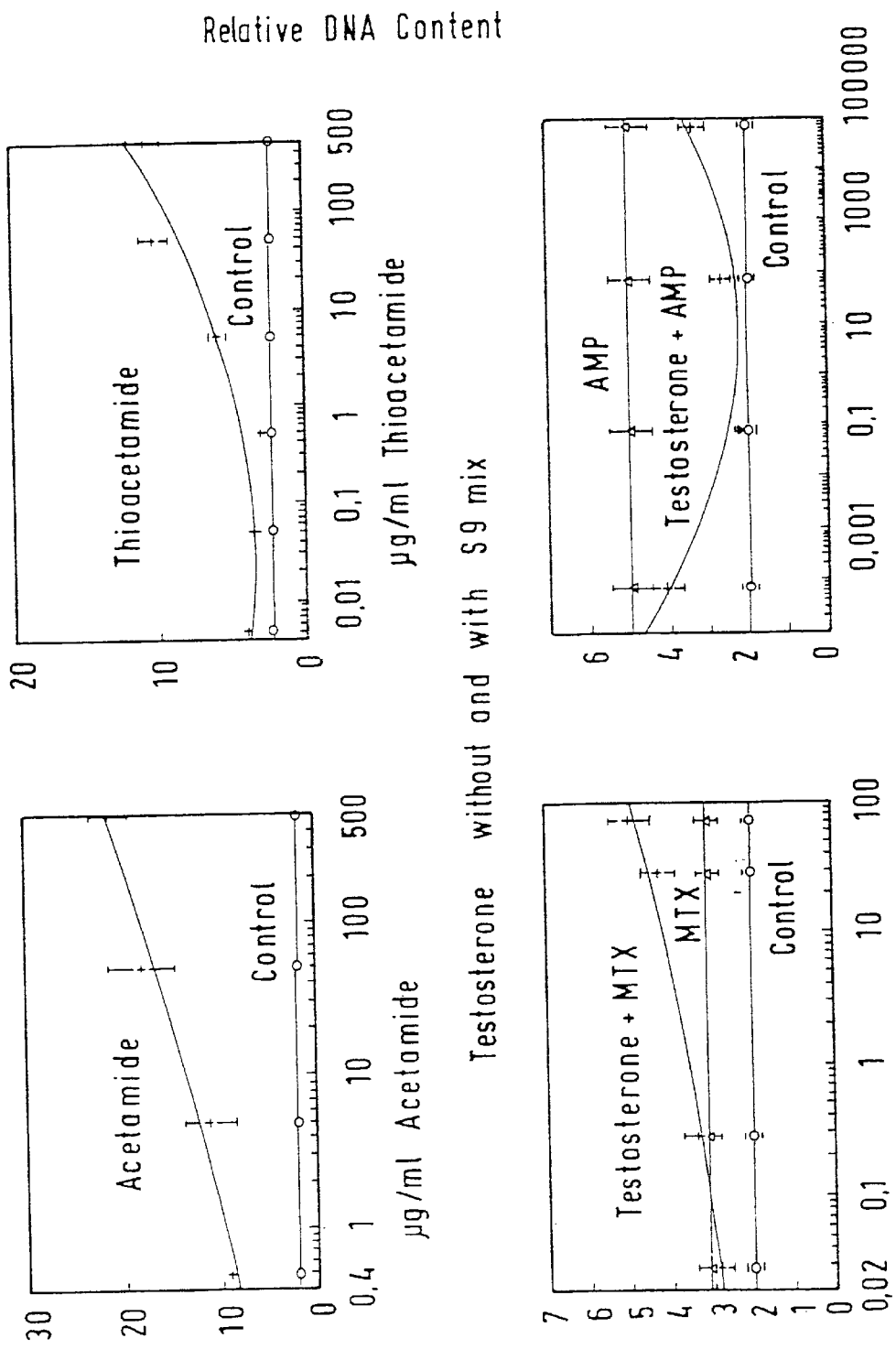
FIG. 3 shows the DNA amplification in cells from Chinese Hamster using non-genotoxic carcinogens and using testosterone with and without S9 mix.
Figure 4:
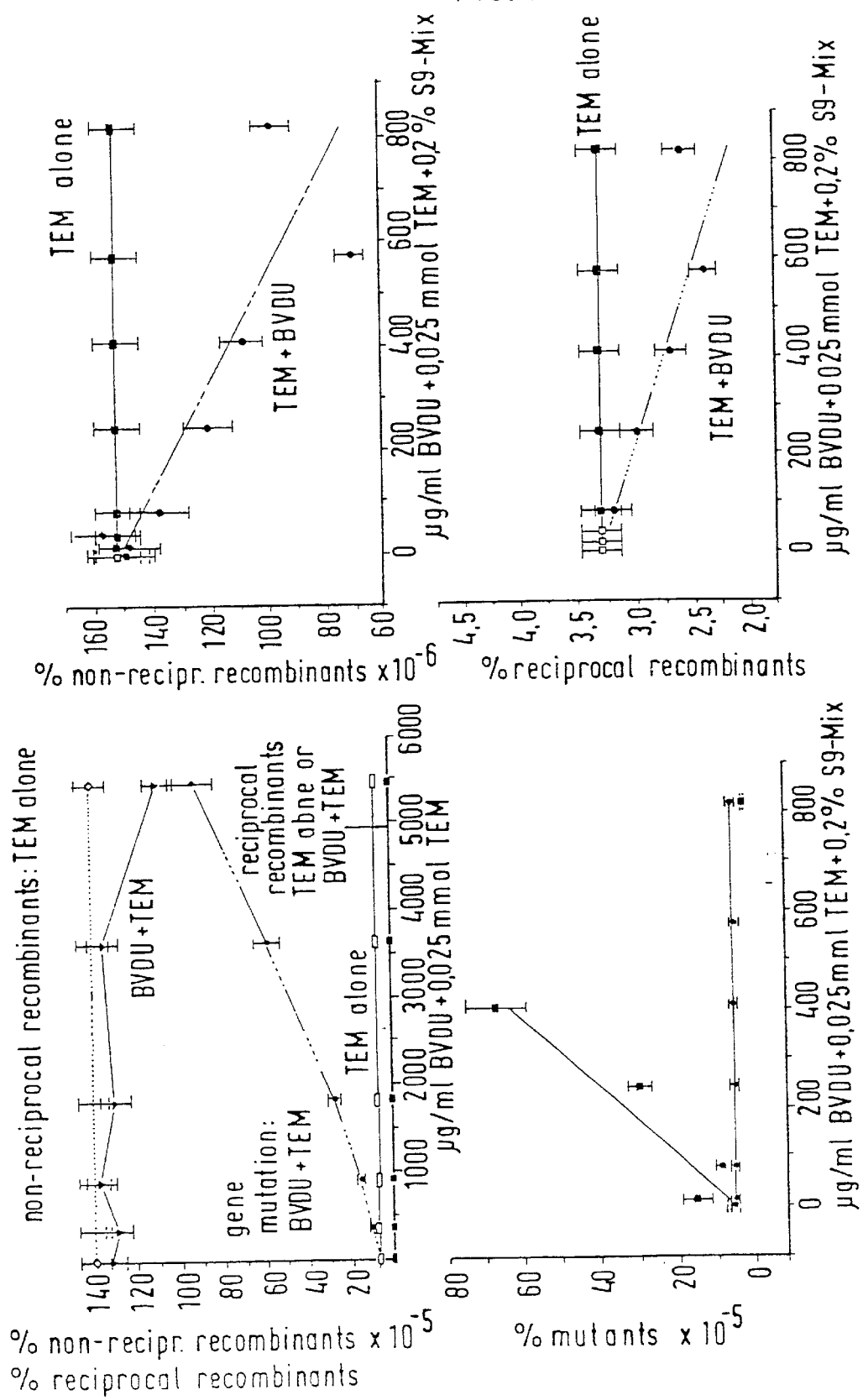
FIG. 4 shows the anti-recombinogenic and co-mutagenic effect of BVDU in experiments with yeast.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

The present invention provides a method and composition for preventing or reducing resistance formation by simultaneous administration of 5' substituted nucleosides and a cytostatic agent. It has become surprisingly apparent that 5' nucleosides prevent or at least attenuate the occurrence of carcinogen-induced gene amplifications. This offers the possibility of preventing the occurrence of resistances against these drugs and also of influencing the degree of malignancy by means of simultaneous administration of these nucleosides with a cytostatic agent.

The following are presented as non-limiting examples of 5' nucleosides: 5-(2-bromovinyl-2'-deoxyuridine (BVDU), (E)-5-(2-bromovinyl)-1-β-D-arabinofuranosyluracil, (E)-5-(2-bromovinyl-2'-deoxy-4'-thiouridine, 5-iodo-2'-deoxycytidine, 5-iodo-2'-deoxyuridine, and 2'-deoxy-5-trifluoromethyluridine. Particularly preferred are BVDU and (E)-5-(2-bromovinyl-) uracil (BVU). BVDU may be used in its salt form, in a protected form or in a prodrug form. A non-limiting example of the prodrug form of BVDU is represented by the formula:

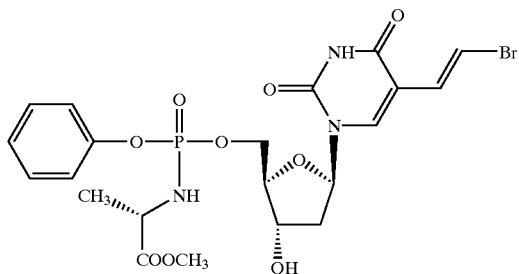

The invention further relates to drugs for preventing resistance formation against cytostatic treatment, said drugs containing 5' nucleosides. The 5' nucleosides are contained in the formulation of the drug in a quantity from which there results a concentration of 0.02 μg/ml to 10 μg/ml in the blood. It is shown in experiments that the optimal range lies at 0.05 μg/ml to 5 μg/ml.

The cytostatic agents can be contained in the formulation in the normal concentrations which are known to those skilled in the art and are available from the Physicians Desk Reference (54th Edition 2000). See also Oshiro, Y., Piper, C. E., Balwierz, P. S., and Garriot, M. L., "Genotoxic Properties of (E)-5(2-bromovinyl)-2'-deoxyuridine (BVDU)", *Fundamental and Applied Toxicology*, 18, 491–498 (1992). Examples of cytostatic agents include cyclophosphamide and other alkylating agents, anti-metabolites such as methotrexate, alkaloids such as vinblastin, antibiotics such as bleomycin, cisplatin and other materials. Other examples of cytostatic agents are disclosed in "Red List 1995", Editio Cantor Verlag für Medizin und Naturwissenschaften, Aulendorf/Württ., 1995.

Examples of cytostatic (antineoplastics) agents include, but are not limited to, alkylating agents such as bisulfan, which is a difunctional alkylating agent chemically known as 1,4 butanediol dimethane sulfonate, carboplatin (platinum, diammine [1,1-cyclobutane-dicarboxlator(2-)-0, 0']), cisplatin (cis-diamminedichloroplatinum), or thiopeta (aziridine, 1,1',1"-phosphinothioylidynetris). Other alkylating agents include nitrogen mustards such as melphalan (L-phenylalanine mustard), cyclophosphamide, ifosfamide, chloroambucil, mechlorethamine HCl, and the like. Other alkylating agents include mitrosoureas such as carmustine, lomustine, polifeprosan 20, streptozocin sterile powder, and the like.

Other examples of cytostatic (antineoplastic) agents include antibiotics such as doxorubicin hydrochloride, bleomycin sulfate, daunorubicin HCl, diactinomycin, daunorubicin citrate, doxorubicin HCl, idarubicin HCl, plicanycin, mitomycin, pentostatin, mitoxantrone, doxorubicin hydrochloride, valrubicin, and the like.

Other examples of cytostatic (antineoplastic) agents include antimetabolites such as cytarabine, fludarabine phosphate, floxuridine, cladribine, methotrexate, mercaptopurine, thioguanine, capecitabine, and the like.

Further examples of cytostatic (antineoplastic) agents include hormonal agonists/antagonists such as androgens, antiandrogens, antiestrogens, estrogen and nitrogen combinations, estrogens, gonadotropin releasing hormone (GNRH) analogues, and immunomudulators. Androgens include, but are not limited to, methyltestosterone, nilutamide, testolactone, and the like. Antiandrogens include, but are not limited to, bicalutamide, flutamide, and the like. Antiestrogens include, but are not limited to anastrozole, toremifene citrate, tamoxifen citrate, and the like. An estrogen and nitrogen combinations include estramustine phosphate sodium. Estrogens include ethinyl estradiol, esterified estrogen, conjugated estrogen (PREMARIN®), and the like. GNRH analogues include leuprolide acetate, goserelin acetate, and the like. Progestins include medroxyprogesterone acetate, magestrol acetate, and the like.

Further examples of cytostatic (antineoplastic) agents include immunomodulators such as levamisole hydrochloride, aldesleukin, and the like.

Still further examples of cytostatic (antineoplastic) agents include those known for adjunct antineoplastic therapy such as allopurinol sodium, dolasetron mesylate, pamidronate disodium, etidronate disodium, fluconazole, erythropoietin, levamisole hydrochloride, amifostine, granisetron hydrochloride, leucovorin, sargramostim, dronabinol, 2-mercaptoethane sulfonate, filgrastim, octreotide acetate, pilocarpine hydrochloride, dexrazoxane, ondansetron hydrochloride, and the like.

Still further examples of cytostatic (antineoplastic) agents include irinotecan hydrochloride, dacarbazine, asparaginase, etoposide phosphate, gemcitabine HCl, trastuzumab, altretamine, topotecan hydrochloride, hydroxyurea, mitotane, interferon alfa-2b, procarbazine hydrochloride, vinorelbine tartrate, pegaspargase, vincaleukoblastine, 22-oxo, sulfate (1:1)(salt), denileukin diftitox, rituximab, aldesleukin, interferon alfa-2a, docetaxel, paclitaxel, BCG Live (Intravesical) also known as TheraCys®, BCG Live also known as TICE®, vinblastine sulfate, etoposide, teniposide, tretinoin, and the like.

Still further examples of cytostatic (antineoplastic) agents include steroids and combinations such as cortisone acetate, dexamethasonel, dexamethasone acetate, betamethasone sodium phosphate and betamethasone, hydrocortisone, hydrocortisone sodium phosphate, prednisolone sodium phosphate, prednisolone, methylprednisolone sodium succinate and the like.

Carriers, additives and auxiliary materials are well known to those of ordinary skill in the art. The composition itself can be prepared as a solid or a liquid form, or also as a spray.

The invention is explained in more detail in the following with reference to model experiments.

EXAMPLE 1

Model Substances

To investigate the amplification phenomena, a hamster cell strain is used which contains a virus (simian virus 40) integrated in the genome. It is known for this cell strain that an addition of genotoxic substances, but also various "non-genotoxic" carcinogens and tumor inducers, leads to amplification of SV40-DNA in the hamster genome. The method is based on the fact that marked SV40-DNA with hamster cell-DNA containing SV40-DNA in an amplified number, serving as a probe, is hybridized. The quantity of bound probe gives an insight into the degree of amplification of the integrated virus-DNA.

In order to determine the degree of amplification, the albumin-gene-DNA is measured simultaneously with the SV40-DNA. The albumin-gene, as opposed to SV40-DNA, is not amplified in the cell. Accordingly the value of the relative SV40-DNA content results from the quotient of the signal of the DNA probe hybridized with SV40-DNA to the signal of the DNA probe hybridized with albumin gene from the same SV40 transformed embryonic CO631 hamster cells.

The following serves as model substances:
1. Mutagens and recombinogenic genotoxic carcinogens (positive control)
   Triethylenmelamin (TEM) 4-Nitrochinolin 1-oxide (4-NQO)
2. Non-carcinogens (negative-control), which induce neither mutations nor recombinations
   acetone
   dimethylformamide
3. Co-recombinogenic Tumor-Inducers
   mezerein
   12-0-tetradecanoyl-phorbol-13-acetate (TPA)
   chrysarobin
   coumarin
4. Recombinogenic non-genotoxic carcinogens with unknown effective mechanism
   thioacetamide
   acetamide
5. Testosterone after metabolization by rat liver microsomes (S9-Mix) and without S9-Mix
   testosterone acts
   with S9-Mix anti-recombinogen and
   without S9-Mix co-recombinogen The effect of the above named model substances alone or in combination with a carcinogen is tested in the gene amplification system.

The results with the model substances are shown in FIGS. 1 to 3.

The non-carcinogens acetone and dimethylfornamide reveal no effect.

All other substances, the non-genotoxic carcinogens with unknown effective mechanism, thioacetamide and acetamide, the genotoxic carcinogens TEM and 4-NQO and the tumor inducers mezerein, 12-0-tetradecanoyl-phorbol-13-acetate (TPA), chrysarobin and coumarin, given alone, increase the SV40 gene amplification.

Experiments with S9-mix reduces the amplifying effect of methotrexate (MTX), and without S9-mix it increases the amplifying effect of amino-6-mercaptopurine (AMP).

These results show an agreement between the initiation of recombination and SV40 gene amplification.

EXAMPLE 2

Inhibition of Carcinogen-induced Gene Amplification by (E)-5-(2-Bromovinyl-)-2'-deoxyuridine (BVDU)

The results are assembled in FIGS. 4 to 7.

In experiments with yeast (FIG. 4), BVDU exhibits an anti-recombinogenic and co-mutagenic effect. This effect is more visible in the presence of liver microsomes (S9-mix) in lower concentration than in the absence of S9-mix, and is also much more defined. Thus metabolisation of BVDU reinforces the anti-recombinogenic effect.

Figure 5:
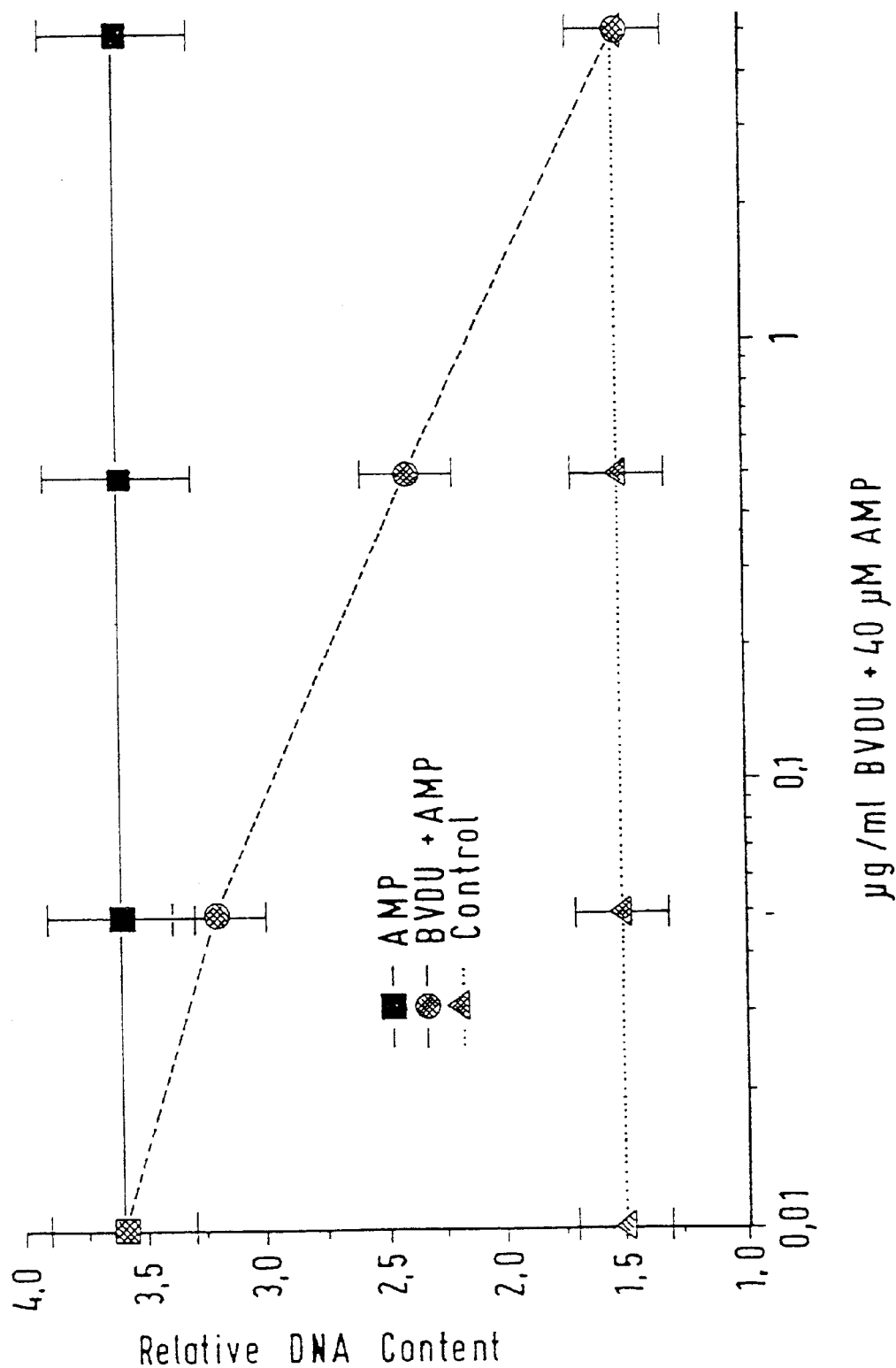
FIG. 5 shows the effect of BVDU on the presence of AMP.

BVDU exhibits, in clinically relevant doses, an inhibition of AMP-induced gene amplification. The effect starts at about 0.05 µg/ml and, dependent on dose, leads at 5 µg/ml to total inhibition of the AMP-induced gene amplification (FIG. 5).

Figure 6:
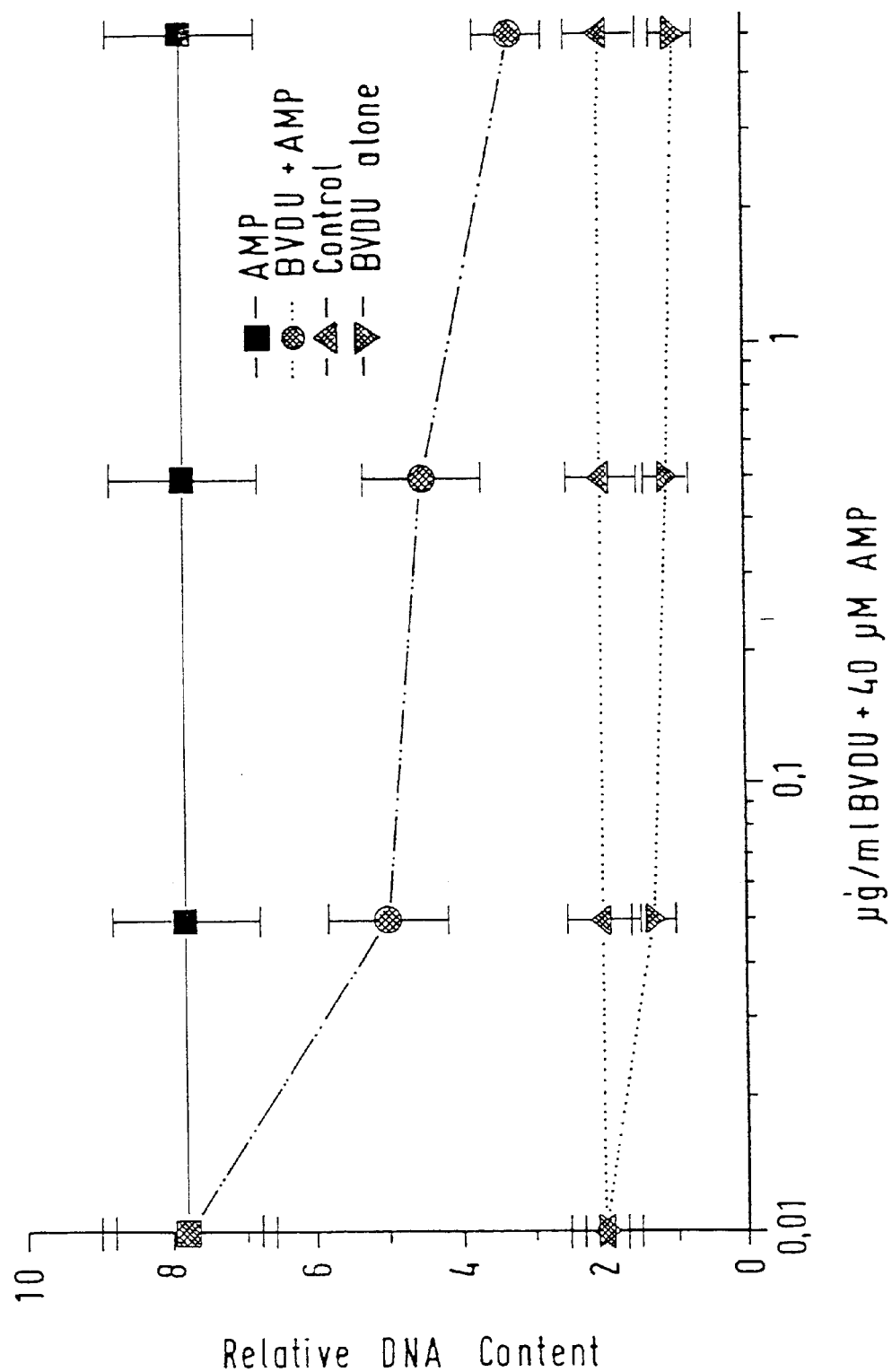
FIG. 6 shows the results of an experiment similar to that shown in FIG. 5, except that BVDU alone is tested as well.

The independent repeat experiment confirms the result (FIG. 6). In addition, BVDU alone appears slightly to lessen the spontaneous degree of amplification.

Figure 7:
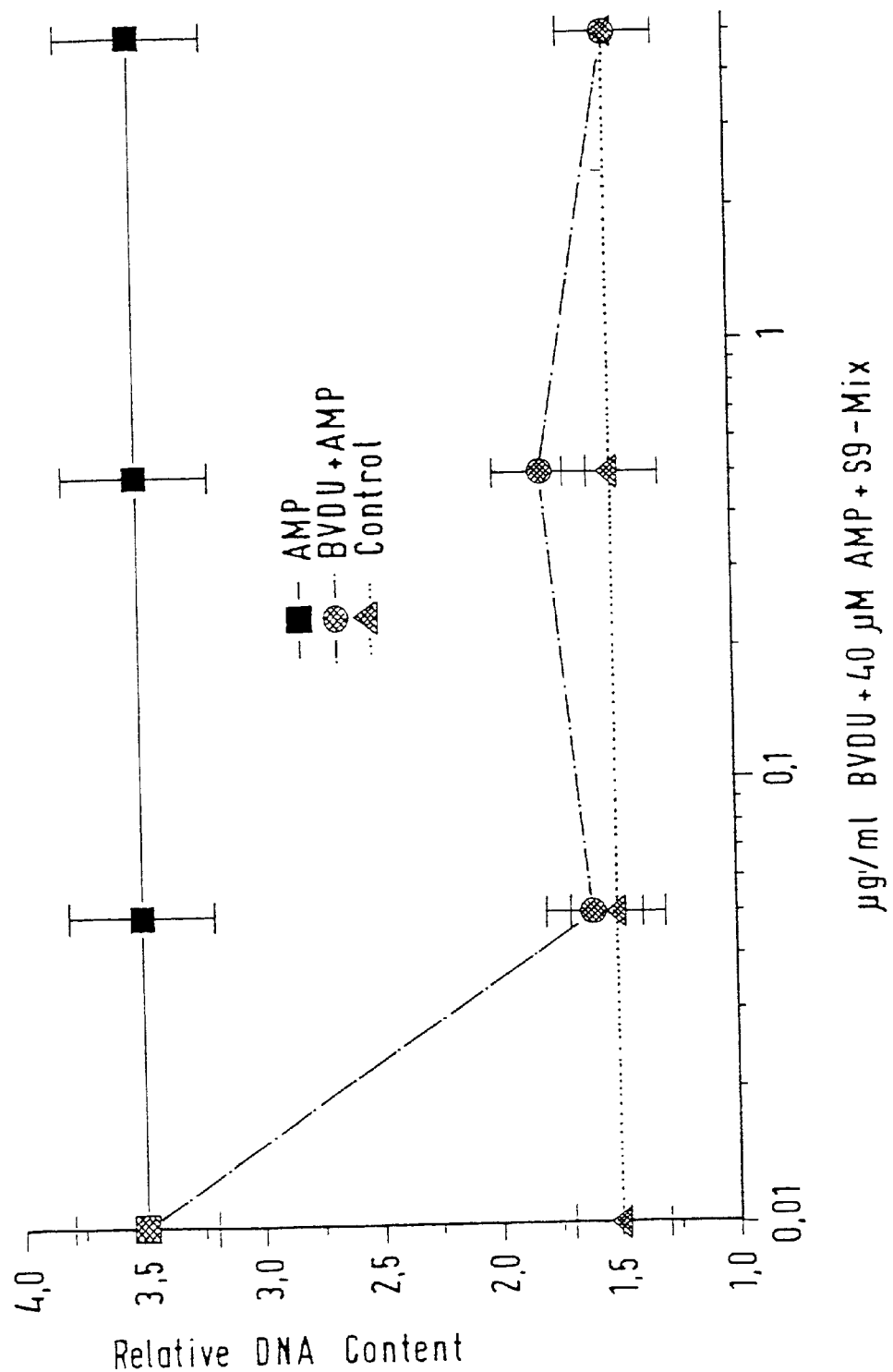
FIG. 7 shows the results of an experiment similar to that shown in FIG. 5, except that S9-mix is also added.

The addition of S9-mix likewise produces a lowering of AMP-induced gene amplification. However, this occurs in a lower dose range than in the experiments without S9-mix. Possible metabolisation of BVDU thus appears further to reinforce the amplification-inhibiting effect (FIG. 7). This appears to further underline the relevance of the results.

In summary it can be stated that BVDU inhibits carcinogen-induced gene amplification. This opens up the possibility, with simultaneous administration of BVDU with a cytostatic agent, of preventing the occurrence of resistances to this drug and of reducing malignancy.

EXAMPLE 3

Figure 8:
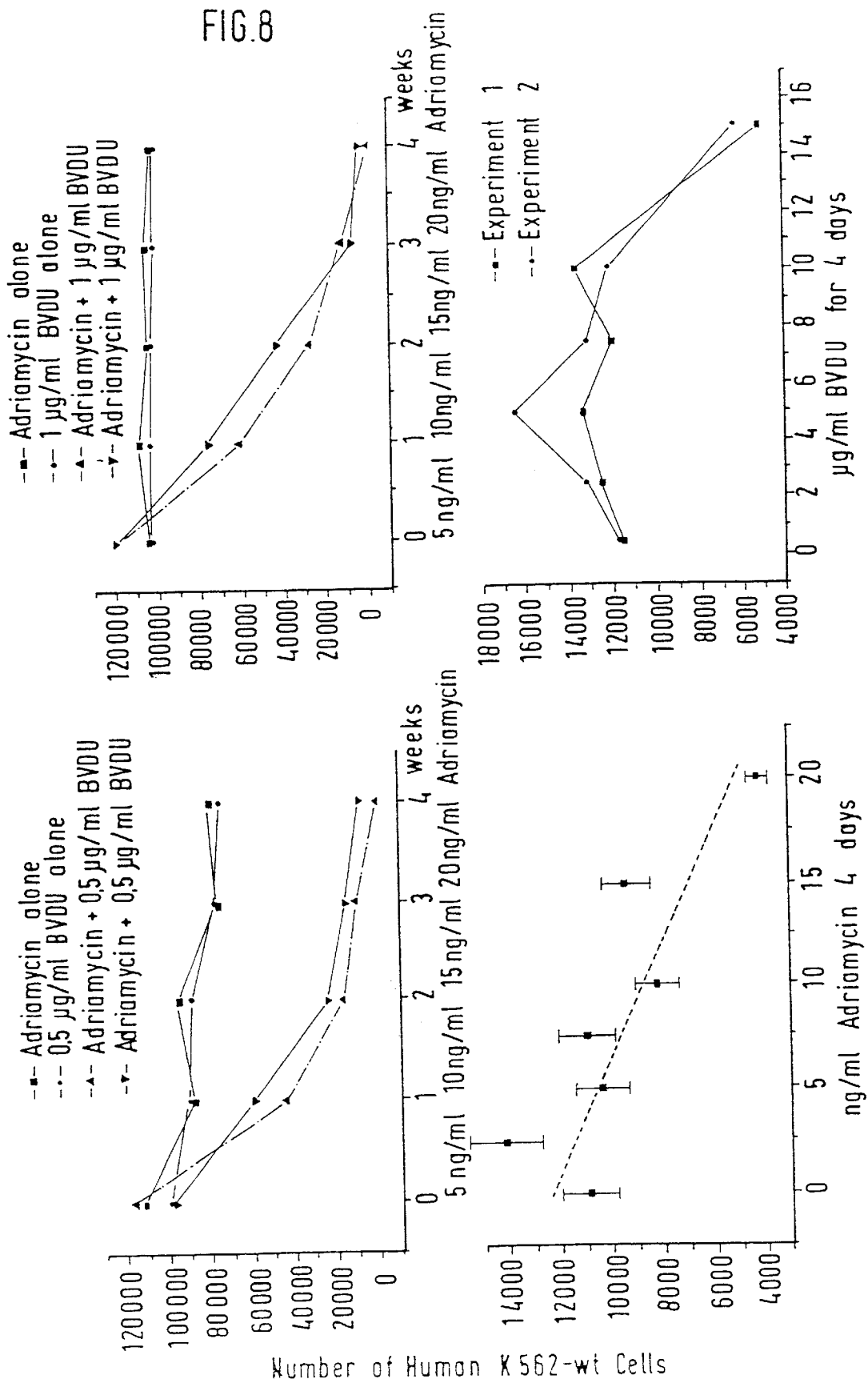
FIG. 8 shows the effect of BVDU on adriamycin in human tumor cell strain K562-WT.
Figure 9:
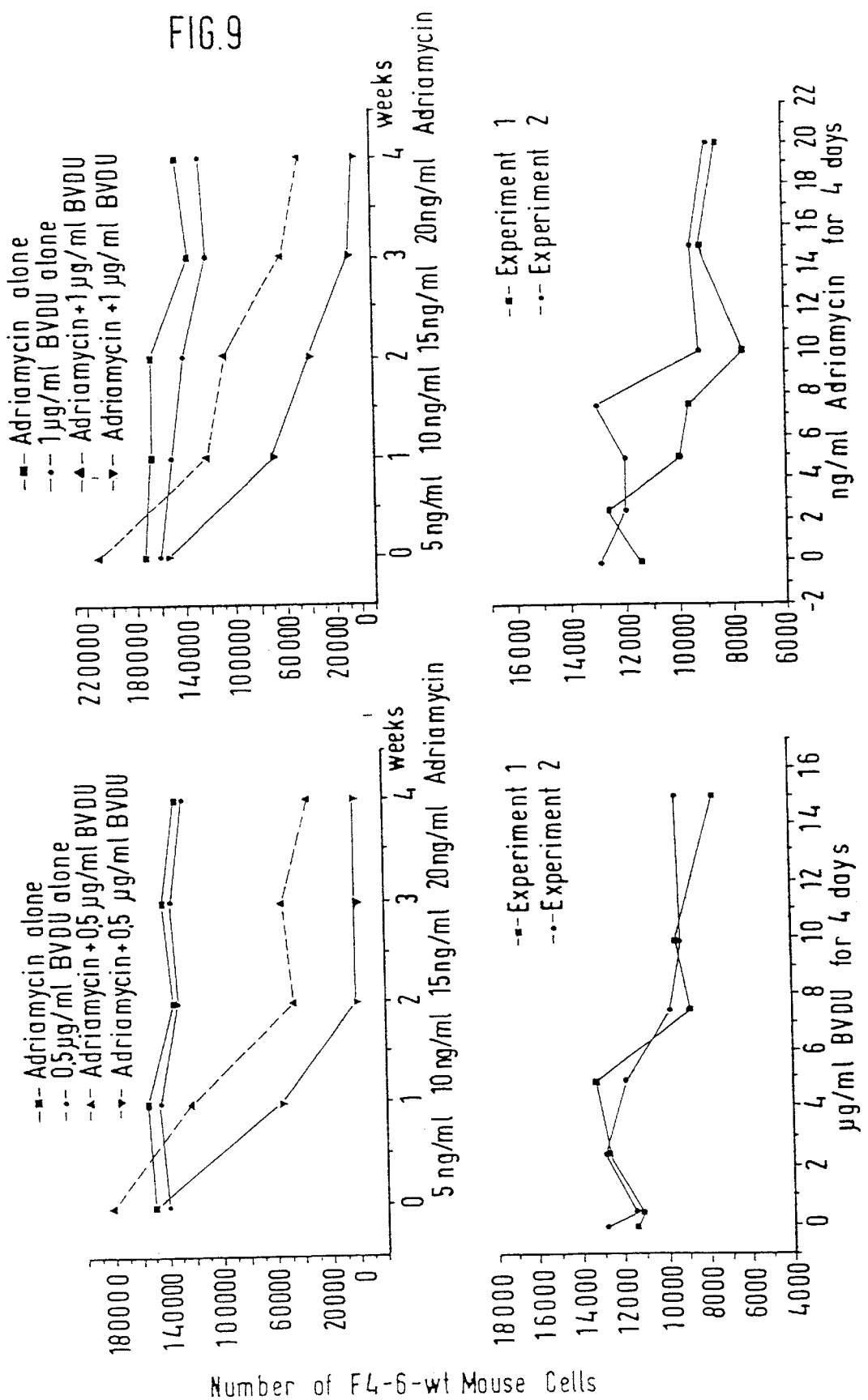
FIG. 9 shows the effect of BVDU on adriamycin in mouse tumor cell strain F46-WT.
Figure 10:
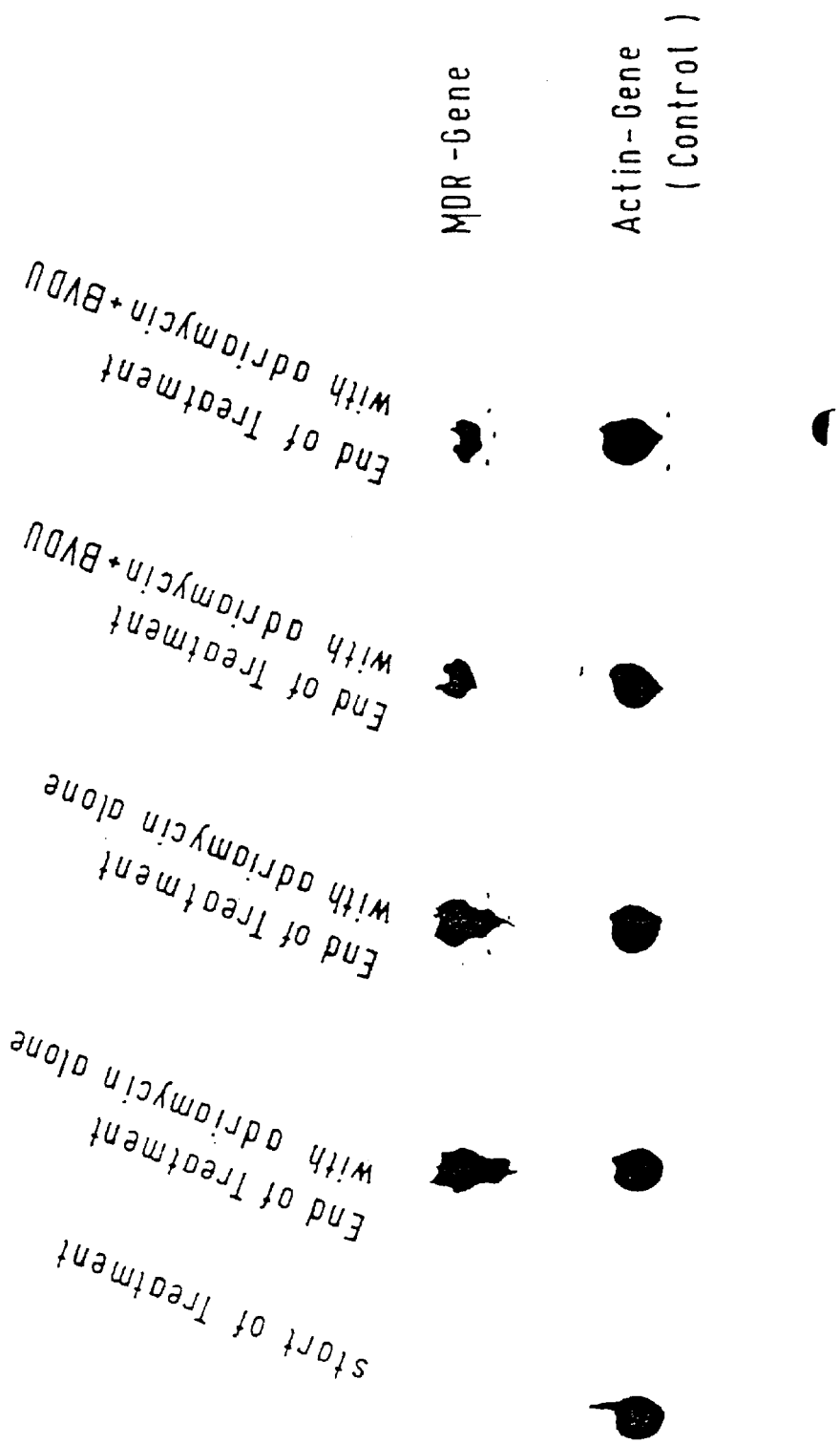
FIG. 10 shows a representation of a Northern Blot which demonstrates the amplification of the MDR gene in F46-WT cells, wherein the MDR gene was used as a probe.

Prevention of the Formation of "Multi-drug Resistance" (MDR) in Human and Animal Tumor Cells to Treatment With Cytostatic Agents by Simultaneous Administration of BVDU The human tumor cell strain K562-WT (FIG. 8) and the tumor cell strain F46-WT of the mouse (FIG. 9) (WT=wild type=sensitive to cytostatic treatment=no amplification of the MDR-gene) is treated over several weeks with staged increase in concentrations of adriamycin. During the treatment the cells acquire a resistance to this treatment. With non-resistant cells, 20 ng/ml adriamycin at a treatment time of 4 days has a severely toxic effect—the cells after long term treatment with staged increase in concentration become totally insensitive to 20 ng/ml adriamycin (FIGS. 8 and 9). The formation of resistance is based on the amplification of the MDR gene. This is indicated with the aid of the Northern Blotting Technique, a method for indicating RNA molecules, i.e., the transcription of a gene, using the MDR gene as a probe (FIG. 10). Resistant cells show a band; non-resistant cells (condition at the start of treatment) show no band.

In parallel experiments with adriamycin with either 0.5 or 1 µg/ml BVDU given together (BVDU acts in human tumor cells only from about 10 µg/ml in a toxic manner, and in mouse cells from about 8 µg/ml (FIGS. 8 and 9)), BVDU prevents the formation of resistance to adriamycin. The tumor cells remain sensitive to the cytostatic treatment and die off. The effect of BVDU is so intense that the treatment must be interrupted by rest stages (growth without substances), so that the experiment extends over 6 to 8 weeks.

BVDU+adriamycin treatment leads to a considerably weaker amplification of the MDR gene than adriamycin treatment alone (FIG. 10). The effect of the BVDU treatment is in reality much greater than is expressed by the attenuation of the band. At the end of the treatment, there remain only cells which have acquired at least a certain resistance to the adriamycin treatment. The cells which have remained non-resistant as a result of the BVDU treatment have already previously died off. The actual relevant effect, and not detectable with the aid of the Northern Technique, therefore consists in die-off of the non-resistant cells, which is measured in the inactivation curves (FIGS. 8 and 9).

As the formation of resistance to cytostatic treatment in human tumors is likewise based on the amplification of the MDR gene, the combination of BVDU with an optional cytostatic agent offers the possibility of carrying out therapy at low doses and over longer periods of time than previously. Moreover, the prevention of the formation of resistance is of great importance also for other applications.

EXAMPLE 4

Figure 11:
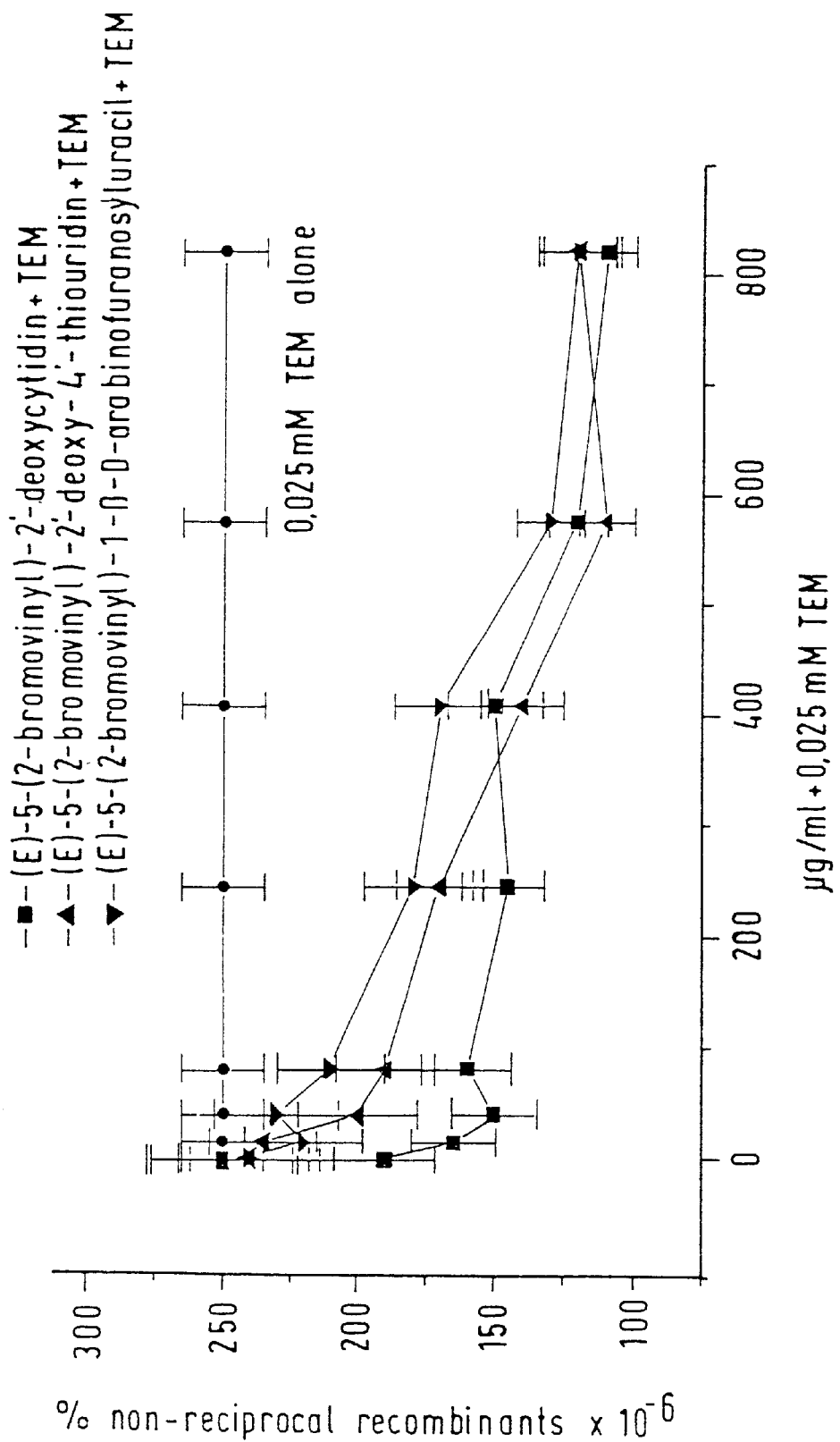
FIG. 11 shows the anti-recombinogenic effects of (E)-5-(2-bromovinyl)-2'-deoxyuridine, (E)-5-(2-bromovinyl)-1-β-D-arabinofuranosyluracil, and (E)-5-(2-bromovinyl)-2'-deoxy-4'-thiouridine in Saccharomyces cerevisiae MP 1.
Figure 12:
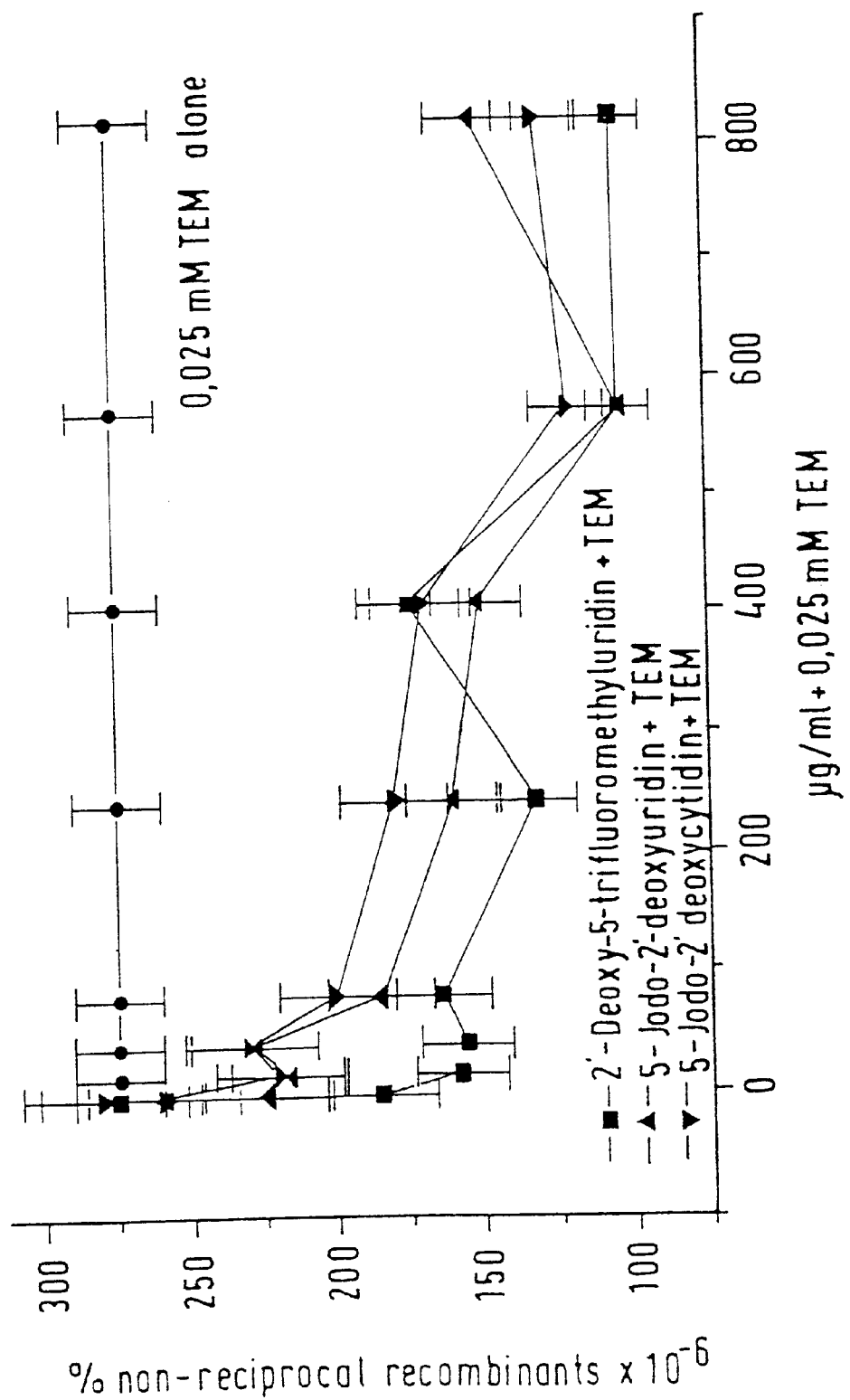
FIG. 12 shows the anti-recombinogenic effects of 5-iodo-2'-deoxycytidine, 5-iodo-2'-deoxyuridine, and 2'-deoxy-5-trifluoromethyluridine in Saccharomyces cerevisiae MP 1.

Prevention of the Formation of "Fulti-drug-resistance" (MDR) in Tumor Cells to Cytostatic Treatment by Simultaneous Administration of Anti-recombinogenic 5' Substituted Nucleosides FIGS. 11 and 12 show that the anti-recombinogenic effect is not specific only to BVDU, but is a property of all 5' substituted nucleosides.

FIG. 11 thus shows the anti-recombinogenic effects of (E)-5-(2-bromovinyl)-2'-deoxyuridine, (E)-5-(2-bromovinyl)-1-β-D-arabinofuranosyl-uracil and (E)-5(2-bromovinyl-2'-deoxy-4'-thiouridine in *Saccharomyces cerevisiae* MP1.

FIG. 12 shows the anti-recombinogenic effects of 5-iodo-2'-deoxycytidine, 5-iodo-2'-deoxyuridine and 2'-deoxy-5-trifluoromethyluridine in *Saccharomyces cerevisiae* MP1.

Figure 13:
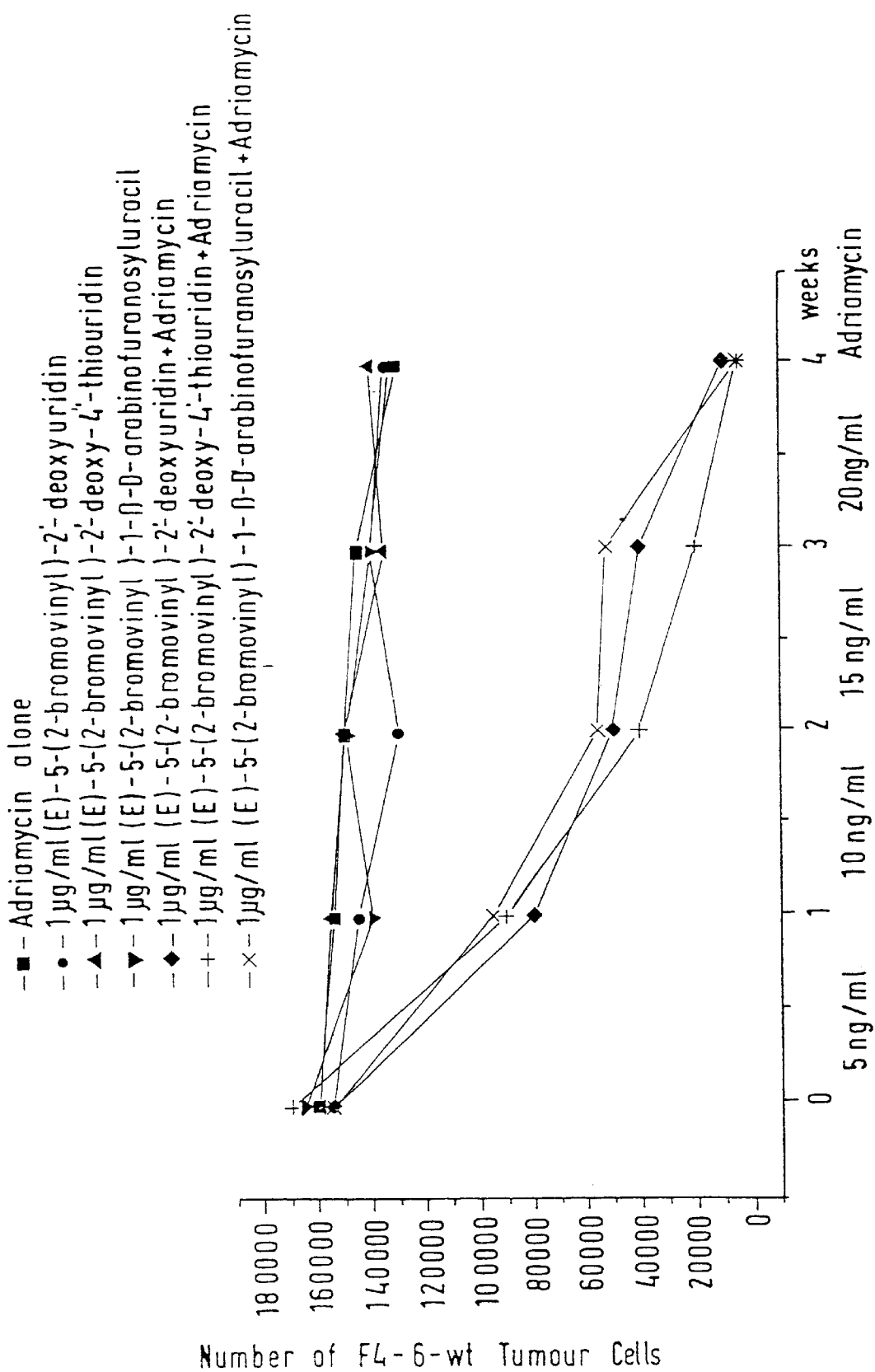
FIG. 13 shows the effect of adriamycin on the mouse tumor cell strain F46-WT alone and in combination with 5' substituted nucleosides.
Figure 14:
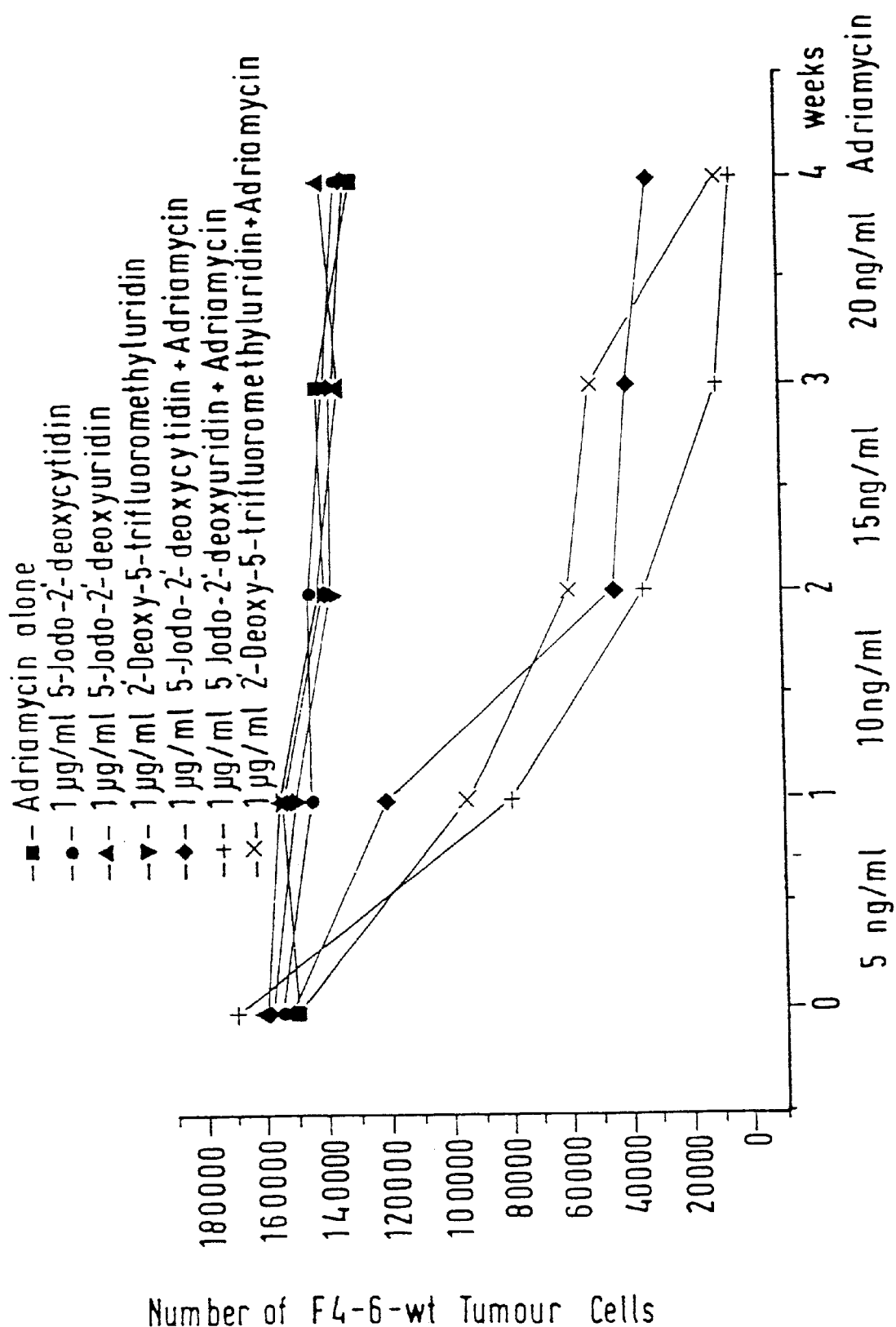
FIG. 14 shows the effect of adriamycin on the mouse tumor cell strain F46-WT alone and in combination with 5' substituted nucleosides.
Figure 15:
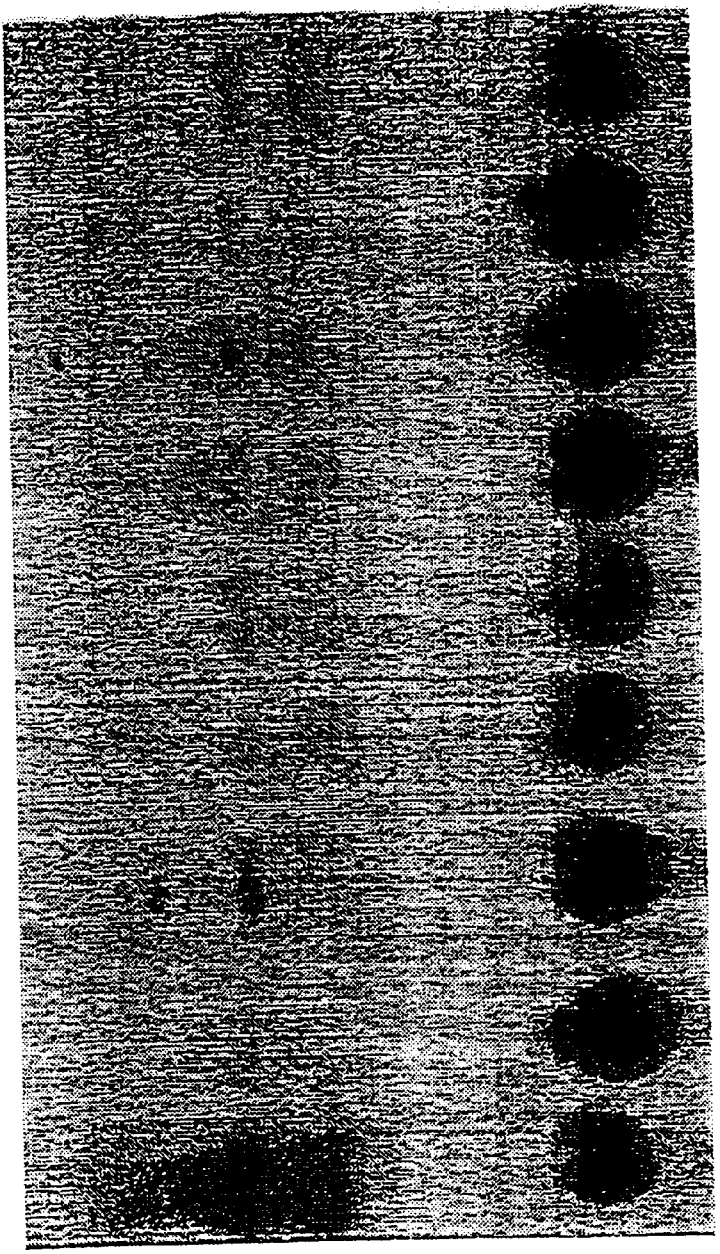
FIG. 15 shows a Northern Blot Analysis of RNA demonstrating the expression of the MDR genes in the mouse tumor cell strain F46-WT.

The tumor cell strain F4-6-WT of the mouse (WT=wild type=sensitive to cytostatic treatment=no amplification of the MDR gene) is treated over several weeks with staged increases in concentration of adriamycin. During the treatment the cells acquire a resistance to this treatment. Whereas 20 ng/ml of adriamycin at a treatment time of 4 days has an extremely toxic effect on non-resistant cells, the cells after a long term treatment with staged increases in concentration become totally insensitive to 20 ng/ml adriamycin (FIGS. 13 and 14). The formation of resistance is based on the amplification of the MDR gene. This is indicated with the aid of the Northern Technique, a method for indicating RNA molecules, i.e., the transcription of a gene, using the MDR gene as a probe (FIG. 15). Resistant cells show a band; non-resistant cells (condition at the start of treatment) show no band. The levels of β-actin MRNA are likewise analyzed as comparison. β-actin is used as an internal control for the RNA quantity.

In parallel experiments, adriamycin is administered with 1 µg/ml of a respective 5' substituted nucleoside. All six 5' substituted nucleosides prevent the formation of resistance to adriamycin. The tumor cells remain sensitive to the cytostatic treatment and die off. The effect of the 5' substituted nucleosides is so intense that the treatment has to be interrupted by rest phases (growth without substances), so that the experiment extends over 6 to 8 weeks.

FIG. 15 shows the Northern Blot Analysis of RNA:

Expression of the MDR genes in the tumor cell strain F4-6WT of the mouse. The levels of β-actin mRNA are likewise also analyzed for comparison. β-actin is used as an internal control for the RNA quantity.

The lanes are labeled as follows:

pos.=adriamycin-resistant F4-6-WT cells neg.=adriamycin-sensitive F4-6-WT cells

1 = 1 µg/ml (E)-5-(2-bromovinyl)-2'-deoxyuridine + adriamycin
2 = 1 µg/ml (E)-5-(2-bromovinyl)-1-β-D-arabinofuranosyl-uracil + adriamycin
3 = 1 µg/ml (E)-5-(2-bromovinyl)-2'-deoxy-4'-thiouridine + adriamycin
4 = 1 µg/ml 5-iodo-2'-deoxycytidine + adriamycin
5 = 1 µg/ml 5-iodo-2'deoxyuridine + adriamycin
6 = 1 mg/ml 2'-deoxy-5-trifluoromethyluridine + adriamycin
7 = 1 µg/ml (E)-5-(2-bromovinyl-)-2'-deoxyuridine (BVDU) + adriamycin 5' substituted nucleoside+adriamycin treatment leads to a considerably weaker amplification of the MDR gene than adriamycin treatment alone (FIG. 15). The effect of the treatment is in reality much more intense than is expressed by the attenuation of the bands. At the end of the treatment, namely, only cells remain which have acquired at least a certain resistance to the adriamycin treatment. The cells which have remained non-resistant due to the BVDU treatment have already previously died off. The actually relevant effect, and not detectable with the aid of the Northern Technique, therefore consists in the die-off of the non-resistant cells, which is measured in the inactivation curves (FIGS. 13 and 14).

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A composition for preventing or reducing the formation of resistance in cytostatic treatment comprising:
(E)-5-(2-bromovinyl-)2'-deoxyuridine (BVDU), or a salt thereof, or BVDU in protected form or prodrug form, and
at least one cytostatic agent, which is an anti-carcinogenic agent and which is not 5-fluorouracil,
wherein the quantity of BVDU is effective to produce a concentration of 0.02 µg/ml to 10 µg/ml in blood, and the at least one cytostatic agent comprises alkylating agents selected from one or more of bisulfan, carboplatin, cisplatin, melphalan, cyclophosphamide, ifosfamide, chloroambucil, mechlorethamine HCl, carmustine, lomustine, polifeprosan 20 or streptozocin sterile powder.

2. The composition of claim 1, wherein the quantity of BVDU, or a salt thereof, or BVDU in protected form or prodrug form is effective to produce a concentration of BVDU of 0.05 µg/ml to 5 µg/ml in blood.

3. A composition for preventing or reducing the formation of resistance in cytostatic treatment comprising:
(E)-5-(2-bromovinyl-)2'-deoxyuridine (BVDU), or a salt thereof, or BVDU in protected form or prodrug form, and
at least one cytostatic agent, which is an anti-carcinogenic agent and which is not 5-fluorouracil,
wherein the quantity of BVDU is effective to produce a concentration of 0.02 µg/ml to 10 µg/ml in blood, and the at least one cytostatic agent comprises antibotics selected from one or more of doxorubicin hydrochloride, bleomycin sulfate, daunorubicin HCl, diactinomycin, daunorubicin citrate, idarubicin HCl, plicamycin, mitomycin, pentostatin, mitoxantrone, or valrubicin.

4. A composition for preventing or reducing the formation of resistance in cytostatic treatment comprising:
(E)-5-(2-bromovinyl-)2'-deoxyuridine (BVDU), or a salt thereof, or BVDU in protected form or prodrug form, and
at least one cytostatic agent, which is an anti-carcinogenic agent and which is not 5-fluorouracil,
wherein the quantity of BVDU is effective to produce a concentration of 0.02 µg/ml to 10 µg/ml in blood, and the at least one cytostatic agent comprises hormonal agonists/antagonists selected from one or more of androgens, antiandrogens, antiestrogens, estrogen and nitrogen combinations, estrogens, gonadotropin releasing hormone (GNRH) analogues, progestins or immunomudulators.

5. The composition of claim 4, wherein the hormonal agonists/antagonists are androgens and the androgens are selected from one or more of methyltestosterone, nilutamide, or testolactone.

6. The composition of claim 4, wherein the hormonal agonists/antagonists are antiandrogens and the antiandrogens are selected from one or more of bicalutamide or flutamide.

7. The composition of claim 4, wherein the hormonal agonists/antagonists are antiestrogens and the antiestrogens are selected from one or more of anastrozole, toremifene citrate, or tamoxifen citrate.

8. The composition of claim 4, wherein the hormonal agonists/antagonists are estrogen and nitrogen combinations and the estrogen and nitrogen combinations is estramustine phosphate sodium.

9. The composition of claim 4, wherein the hormonal agonists/antagonists are estrogens and the estrogens are selected from one or more of ethinyl estradiol, esterified estrogen, or conjugated estrogen.

10. The composition of claim 4, wherein the hormonal agonists/antagonists are GNRH analogues and the GNRH analogues are selected from one or more of leuprolide acetate or goserelin acetate.

11. The composition of claim 4, wherein the hormonal agonists/antagonists are progestins and the progestins are selected from one or more of medroxyprogesterone acetate or magestrol acetate.

12. The composition of claim 4, wherein the hormonal agonists/antagonists are immunomodulators and the immunomodulators are selected from one or more of levamisole hydrochloride or aldesleukin.

13. A composition for preventing or reducing the formation of resistance in cytostatic treatment comprising:
(E)-5-(2-bromovinyl-)2'-deoxyuridine (BVDU), or a salt thereof, or BVDU in protected form or prodrug form, and
at least one cytostatic agent, which is an anti-carcinogenic agent and which is not 5-fluorouracil,
wherein the quantity of BVDU is effective to produce a concentration of 0.02 µg/ml to 10 µg/ml in blood, and the at least one cytostatic agent is selected from one or more of allopurinol sodium, dolasetron mesylate, pamidronate disodium, etidronate disodium, fluconazole, erythropoietin, levamisole hydrochloride, amifostine, granisetron hydrochloride, leucovorin, sargramostim, dronabinol, 2-mercaptoethane sulfonate, filgrastim, octreotide acetate, pilocarpine hydrochloride, dexrazoxane, ondansetron hydrochloride, irinotecan hydrochloride, dacarbazine, asparaginase, etoposide phosphate, gemcitabine HCl, trastuzumab, altretamine, topotecan hydrochloride, hydroxyurea, mitotane, interferon alfa-2b, procarbazine hydrochloride, vinorelbine tartrate, pegaspargase, vincaleukoblastine, 22-oxo, sulfate (1:1)(salt), denileukin diftitox, rituximab, aldesleukin, interferon alfa-2a, docetaxel, paclitaxel, BCG Live (Intravesical), BCG Live, vinblastine sulfate, etoposide, teniposide, or tretinoin.

14. A composition for preventing or reducing the formation of resistance in cytostatic treatment comprising:
(E)-5-(2-bromovinyl-)2'-deoxyuridine (BVDU), or a salt thereof, or BVDU in protected form or prodrug form, and
at least one cytostatic agent, which is an anti-carcinogenic agent and which is not 5-fluorouracil,
wherein the quantity of BVDU is effective to produce a concentration of 0.02 µg/ml to 10 µg/ml in blood, and the at least one cytostatic agent comprises steroids and combinations selected from one or more of cortisone acetate, dexamethasonel, dexamethasone acetate, betamethasone sodium phosphate and betamethasone sodium phosphate and betamethasone, hydrocortisone, hydrocortisone sodium phosphate, prednisolone sodium phosphate, prednisolone or methylprednisolone sodium succinate.

15. A method of reducing resistance in cytostatic treatment comprising delivering to a host therapeutically-effective amount of at least one cytostatic agent, which is an anti-carcinogenic agent and which is not 5-fluorouracil, and therapeutically-effective amount of BVDU, a salt thereof, or BVDU in protected form or prodrug form.

16. The method of claim 15, wherein the therapeutically-effective amount of BVDU is an amount effective to produce a blood concentration of from about 0.02 µg/ml to about 10 µg/ml.

17. The method of claim 16, wherein the therapeutically-effective amount of BVDU is an amount effective to produce a blood concentration of from about 0.05 µg/ml to about 5 µg/ml.

18. The method of claim 15, wherein the at least one cytostatic agent is selected from alkaloids, alkylating agents, antibiotics, anti-metabolites, hormonal agonists/antagonists or steroids and combinations.

19. A composition for preventing or reducing the formation of resistance in cytostatic treatment comprising:
(E)-5-(2-bromovinyl-)2'-debxyuridine (BVDU), or a salt thereof, or BVDU in protected form or prodrug form, and
at least one cytostatic agent, which is an anti-carcinogenic agent and which is not 5-fluorouracil,
wherein the quantity of BVDU is effective to produce a concentration of 0.02 µg/ml to 10 µg/ml in blood, and the at least one cytostatic agent is adriamycin.

20. The method of claim 18, wherein the at least one cytostatic agent is adriamycin.

21. The method of reducing resistance in cytostatic treatment of claim 18, wherein the at least one cytostatic agent are alkylating agents and the alkylating agents are selected from one or more of bisulfan, carboplatin, cisplatin, melphalan, cyclophosphamide, ifosfamide, chloroambucil, mechlorethamine HCl, carmustine, lomustine, polifeprosan 20 or streptozocin sterile powder.

22. The method of reducing resistance in cytostatic treatment of claim 18, wherein the at least one cytostatic agent are antibiotics and the antibiotics are selected from one or more of doxorubicin hydrochloride, bleomycin sulfate, daunorubicin HCl, diactinomycin, daunorubicin citrate, idarubicin HCl, plicamycin, mitomycin, pentostatin, mitoxantrone, or valrubicin.

23. The method of reducing resistance in cytostatic treatment of claim 18, wherein the at least one cytostatic agent are anti-metabolites and the anti-metabolites are selected from one or more of cytarabine, fludarabine phosphate, floxuridine, cladribine, mercaptopurine, thioguanine, or capecitabine.

24. The method of reducing resistance in cytostatic treatment of claim 18, wherein the at least one cytostatic agent are hormonal agonists/antagonists and the hormonal agonists/antagonists are selected from androgens, antiandrogens, antiestrogens, estrogen and nitrogen combinations, estrogens, gonadotropin releasing hormone (GNRH) analogues, progestins or immunomudulators.

25. The method of reducing resistance in cytostatic treatment of claim 24, wherein the hormonal agonists/antagonists are androgens and the androgens are selected from one or more of methyltestosterone, nilutamide, or testolactone.

26. The method of reducing resistance in cytostatic treatment of claim 24, wherein the hormonal agonists/antagonists are antiandrogens and the antiandrogens are selected from one or more of bicalutamide or flutamide.

27. The method of reducing resistance in cytostatic treatment of claim 24, wherein the hormonal agonists/antagonists are antiestrogens and the antiestrogens are selected from one or more of anastrozole, toremifene citrate, or tamoxifen citrate.

28. The method of reducing resistance in cytostatic treatment of claim 24, wherein the hormonal agonists/antagonists are estrogen and nitrogen combinations and the estrogen and nitrogen combinations is estramustine phosphate sodium.

29. The method of reducing resistance in cytostatic treatment of claim 24, wherein the hormonal agonists/antagonists are estrogens and the estrogens are selected from one or more of ethinyl estradiol, esterified estrogen, or conjugated estrogen.

30. The method of reducing resistance in cytostatic treatment of claim 24, wherein the hormonal agonists/antagonists are GNRH analogues and the GNRH analogues are selected from one or more of leuprolide acetate or goserelin acetate.

31. The method of reducing resistance in cytostatic treatment of claim 24, wherein the hormonal agonists/antagonists are progestins and the progestins are selected from one or more of medroxyprogesterone acetate or magestrol acetate.

32. The method of reducing resistance in cytostatic treatment of claim 24, wherein the hormonal agonists/antagonists are immunomodulators and the immunomodulators are selected from one or more of levamisole hydrochloride or aldesleukin.

33. The method of reducing resistance in cytostatic treatment of claim 18, wherein the at least one cytostatic agent is selected from one or more of allopurinol sodium, dolasetron mesylate, pamidronate disodium, etidronate disodium, fluconazole, erythropoietin, levamisole hydrochloride, amifostine, granisetron hydrochloride, leucovorin, sargramostim, dronabinol, 2-mercaptoethane sulfonate, filgrastim, octreotide acetate, pilocarpine hydrochloride, dexrazoxane, ondansetron hydrochloride, irinotecan hydrochloride, dacarbazine, asparaginase, etoposide phosphate, gemcitabine HCl, trastuzumab, altretamine, topotecan hydrochloride, hydroxyurea, mitotane, interferon alfa-2b, procarbazine hydrochloride, vinorelbine tartrate, pegaspargase, vincaleukoblastine, 22-oxo, sulfate (1:1) (salt), denileukin diftitox, rituximab, aldesleukin, interferon alfa-2a, docetaxel, paclitaxel, BCG Live (Intravesical), BCG Live, vinblastine sulfate, etoposide, teniposide, or tretinoin.

34. The method of reducing resistance in cytostatic treatment of claim 18, wherein the at least one cytostatic agent are steroids and combinations and the steroids and combinations are selected from one or more of cortisone acetate, dexamethasonel, dexamethasone acetate, betamethasone sodium phosphate and betamethasone, hydrocortisone, hydrocortisone sodium phosphate, prednisolone sodium phosphate, prednisolone or methylprednisolone sodium succinate.

35. A method of reducing resistance in cytostatic treatment comprising delivering to a host therapeutically-effective amount of at least one cytostatic agent, which is not 5-fluorouracil, and therapeutically-effective amount of BVDU, a salt thereof, or BVDU in protected form or prodrug form, wherein the at least one cytostatic agent is selected from one or more of alkaloids, alkylating agents, antibiotics, anti-metabolites, hormonal agonists/antagonists or steroids and combinations.

36. The method of reducing resistance in cytostatic treatment of claim 35, wherein the at least one cytostatic agent is selected from one or more of alkaloids, alkylating agents, antibiotics, anti-metabolites, hormonal agonists/antagonists or steroids and combinations.

37. The method of reducing resistance in cytostatic treatment of claim 36, wherein the at least one cytostatic agent are alkylating agents and the alkylating agents are selected from one or more of bisulfan, carboplatin, cisplatin, melphalan, cyclophosphamide, ifosfamide, chloroambucil, mechlorethamine HCl, carmustine, lomustine, polifeprosan 20 or streptozocin sterile powder.

38. The method of reducing resistance in cytostatic treatment of claim 36, wherein the at least one cytostatic agent are antibiotics and the antibiotics are selected from one or more of doxorubicin hydrochloride, bleomycin sulfate, daunorubicin HCl, diactinomycin, daunorubicin citrate, idarubicin HCl, plicamycin, mitomycin, pentostatin, mitoxantrone, or valrubicin.

39. The method of reducing resistance in cytostatic treatment of claim 36, wherein the at least one cytostatic agent are anti-metabolites and the anti-metabolites are selected from one or more of cytarabine, fludarabine phosphate, floxuridine, cladribine, mercaptopurine, thioguanine, or capecitabine.

40. The method of reducing resistance in cytostatic treatment of claim 36, wherein the at least one cytostatic agent are hormonal agonists/antagonists and the hormonal agonists/antagonists are selected from androgens, antiandrogens, antiestrogens, estrogen and nitrogen combinations, estrogens, gonadotropin releasing hormone (GNRH) analogues, progestins or immunomudulators.

41. The method of reducing resistance in cytostatic treatment of claim 40, wherein the hormonal agonists/antagonists are androgens and the androgens are selected from one or more of methyltestosterone, nilutamide, or testolactone.

42. The method of reducing resistance in cytostatic treatment of claim 40, wherein the hormonal agonists/antagonists are antiandrogens and the antiandrogens are selected from one or more of bicalutamide or flutamide.

43. The method of reducing resistance in cytostatic treatment of claim 40, wherein the hormonal agonists/antagonists are antiestrogens and the antiestrogens are selected from one or more of anastrozole, toremifene citrate, or tamoxifen citrate.

44. The method of reducing resistance in cytostatic treatment of claim 40, wherein the hormonal agonists/antagonists are estrogen and nitrogen combinations and the estrogen and nitrogen combinations is estramustine phosphate sodium.

45. The method of reducing resistance in cytostatic treatment of claim 40, wherein the hormonal agonists/antagonists are estrogens and the estrogens are selected from one or more of ethinyl estradiol, esterified estrogen, or conjugated estrogen.

46. The method of reducing resistance in cytostatic treatment of claim 40, wherein the hormonal agonists/antagonists are GNRH analogues and the GNRH analogues are selected from one or more of leuprolide acetate or goserelin acetate.

47. The method of reducing resistance in cytostatic treatment of claim 40, wherein the hormonal agonists/ antagonists are progestins and the progestins are selected from one or more of medroxyprogesterone acetate or magestrol acetate.

48. The method of reducing resistance in cytostatic treatment of claim 40, wherein the hormonal agonists/antagonists are immunomodulators and the immunomodulators are selected from one or more of levamisole hydrochloride or aldesleukin.

49. The method of reducing resistance in cytostatic treatment of claim 36, wherein the at least one cytostatic agent is selected from one or more of allopurinol sodium, dolasetron mesylate, pamidronate disodium, etidronate disodium, fluconazole, erythropoietin, levamisole hydrochloride, amifostine, granisetron hydrochloride, leucovorin, sargramostim, dronabinol, 2-mercaptoethane sulfonate, filgrastim, octreotide acetate, pilocarpine hydrochloride, dexrazoxane, ondansetron hydrochloride, irinotecan hydrochloride, dacarbazine, asparaginase, etoposide phosphate, gemcitabine HCl, trastuzumab, altretamine, topotecan hydrochloride, hydroxyurea, mitotane, interferon alfa-2b, procarbazine hydrochloride, vinorelbine tartrate, pegaspargase, vincaleukoblastine, 22-oxo, sulfate (1:1) (salt), denileukin diftitox, rituximab, aldesleukin, interferon alfa-2a, docetaxel, paclitaxel, BCG Live (Intravesical), BCG Live, vinblastine sulfate, etoposide, teniposide, or tretinoin.

50. The method of reducing resistance in cytostatic treatment of claim 36, wherein the at least one cytostatic agent are steroids and combinations and the steroids and combinations are selected from one or more of cortisone acetate, dexamethasonel, dexamethasone acetate, betamethasone sodium phosphate and betamethasone, hydrocortisone, hydrocortisone sodium phosphate, prednisolone sodium phosphate, prednisolone or methylprednisolone sodium succinate.

51. The method of reducing resistance in cytostatic treatment of claim 35, wherein the therapeutically-effective amount of BVDU is an amount effective to produce a blood concentration of from about 0.02 $\mu$g/ml to about 10 $\mu$g/ml.

52. The method of reducing resistance in cytostatic treatment of claim 51, wherein the therapeutically-effective amount of BVDU is an amount effective to produce a blood concentration of from about 0.05 $\mu$g/ml to about 5 $\mu$g/ml.

53. The method of reducing resistance in cytostatic treatment of claim 35, wherein the at least one cytostatic agent is adriamycin.

\* \* \* \* \*